United States Patent
Brannan et al.

(10) Patent No.: US 10,813,692 B2
(45) Date of Patent: Oct. 27, 2020

(54) 90-DEGREE INTERLOCKING GEOMETRY FOR INTRODUCER FOR FACILITATING DEPLOYMENT OF MICROWAVE RADIATING CATHETER

(71) Applicant: COVIDIEN LP, Mansfield, MA (US)

(72) Inventors: Joseph D. Brannan, Lyons, CO (US); Eric W. Larson, Littleton, CO (US)

(73) Assignee: COVIDIEN LP, Mansfield, MA (US)

(*) Notice: Subject to any disclaimer, the term of this patent is extended or adjusted under 35 U.S.C. 154(b) by 875 days.

(21) Appl. No.: 15/426,230

(22) Filed: Feb. 7, 2017

(65) Prior Publication Data
US 2017/0245930 A1    Aug. 31, 2017

Related U.S. Application Data

(60) Provisional application No. 62/301,255, filed on Feb. 29, 2016.

(51) Int. Cl.
*A61B 18/18* (2006.01)
*A61B 18/00* (2006.01)

(52) U.S. Cl.
CPC . *A61B 18/1815* (2013.01); *A61B 2018/00011* (2013.01); *A61B 2018/00023* (2013.01);
(Continued)

(58) Field of Classification Search
CPC ............... A61B 18/18; A61B 18/1815; A61B 2018/00011; A61B 2018/00023;
(Continued)

(56) References Cited

U.S. PATENT DOCUMENTS

| D223,367 S | 4/1972 | Kountz |
| D263,020 S | 2/1982 | Rau, III |

(Continued)

FOREIGN PATENT DOCUMENTS

| CA | 2800312 A1 | 11/2011 |
| CA | 2832593 A1 | 7/2012 |

(Continued)

OTHER PUBLICATIONS

European Search Report for corresponding European Application No. 17158082.2 dated Jul. 24, 2017.

(Continued)

*Primary Examiner* — Michael F Peffley
*Assistant Examiner* — Khadijeh A Vahdat

(57) ABSTRACT

A microwave ablation system includes a first cannula, a trocar insertable through the first cannula and configured to facilitate insertion of the first cannula into a target tissue, and a microwave antenna assembly configured to interlock with the first cannula, the microwave antenna assembly including a coaxial feedline having a radiating section formed thereon, the microwave antenna configured to be inserted into the first cannula. The microwave ablation system further includes an actuator operatively connected to one of the first cannula or microwave antenna assembly. Operation of the actuator between a first position and a second position exposes the radiating section of the microwave antenna assembly from a distal portion of the first cannula.

19 Claims, 20 Drawing Sheets

(52) U.S. Cl.
CPC .............. *A61B 2018/00184* (2013.01); *A61B 2018/00577* (2013.01); *A61B 2018/1869* (2013.01)

(58) Field of Classification Search
CPC ........... A61B 2018/00184; A61B 2018/00577; A61B 2018/1869
USPC ..................................................... 606/33–41
See application file for complete search history.

(56) References Cited

U.S. PATENT DOCUMENTS

| | | |
|---|---|---|
| D266,842 S | 11/1982 | Villers et al. |
| D278,306 S | 4/1985 | McIntosh |
| 4,583,589 A | 4/1986 | Kasevich |
| D295,893 S | 5/1988 | Sharkany et al. |
| D295,894 S | 5/1988 | Sharkany et al. |
| 4,846,171 A | 7/1989 | Kauphusman et al. |
| 5,301,687 A | 4/1994 | Wong et al. |
| 5,342,357 A | 8/1994 | Nardella |
| 5,342,393 A | 8/1994 | Stack |
| 5,364,392 A | 11/1994 | Warner et al. |
| 5,370,644 A | 12/1994 | Langberg |
| D354,218 S | 1/1995 | Van de Peer |
| 5,413,571 A | 5/1995 | Katsaros et al. |
| 5,529,067 A | 6/1996 | Larsen et al. |
| 5,540,715 A | 7/1996 | Katsaros et al. |
| 5,545,137 A | 8/1996 | Rudie et al. |
| 5,582,617 A | 12/1996 | Klieman et al. |
| 5,603,697 A | 2/1997 | Grundy et al. |
| 5,624,392 A | 4/1997 | Saab |
| 5,630,833 A | 5/1997 | Katsaros et al. |
| 5,649,959 A | 7/1997 | Hannam et al. |
| 5,685,839 A | 11/1997 | Edwards et al. |
| 5,693,082 A | 12/1997 | Warner et al. |
| 5,741,249 A | 4/1998 | Moss et al. |
| 5,817,119 A | 10/1998 | Klieman et al. |
| 5,846,248 A | 12/1998 | Chu et al. |
| 5,974,343 A | 10/1999 | Brevard et al. |
| 5,980,505 A | 11/1999 | Wilson |
| 5,993,447 A | 11/1999 | Blewett et al. |
| 5,995,875 A | 11/1999 | Blewett et al. |
| 6,014,581 A | 1/2000 | Whayne et al. |
| 6,026,331 A | 2/2000 | Feldberg et al. |
| D424,693 S | 5/2000 | Pruter |
| D424,694 S | 5/2000 | Tetzlaff et al. |
| D425,201 S | 5/2000 | Tetzlaff et al. |
| 6,061,551 A | 5/2000 | Sorrells et al. |
| 6,066,139 A | 5/2000 | Ryan et al. |
| 6,068,627 A | 5/2000 | Orszulak et al. |
| 6,099,550 A | 8/2000 | Yoon |
| 6,106,524 A | 8/2000 | Eggers et al. |
| 6,117,101 A | 9/2000 | Diederich et al. |
| 6,139,527 A | 10/2000 | Laufer et al. |
| 6,186,978 B1 | 2/2001 | Samson et al. |
| 6,188,355 B1 | 2/2001 | Gilboa |
| 6,210,367 B1 | 4/2001 | Carr |
| 6,221,039 B1 | 4/2001 | Durgin et al. |
| 6,235,024 B1 | 5/2001 | Tu |
| 6,239,724 B1 | 5/2001 | Doron et al. |
| 6,277,113 B1 | 8/2001 | Berube |
| D449,886 S | 10/2001 | Tetzlaff et al. |
| 6,352,503 B1 | 3/2002 | Matsui et al. |
| 6,355,016 B1 | 3/2002 | Bagaoisan et al. |
| 6,375,634 B1 | 4/2002 | Carroll |
| D457,958 S | 5/2002 | Dycus et al. |
| D457,959 S | 5/2002 | Tetzlaff et al. |
| 6,398,781 B1 | 6/2002 | Goble et al. |
| 6,413,255 B1 | 7/2002 | Stern |
| 6,419,680 B1 | 7/2002 | Cosman et al. |
| 6,427,089 B1 | 7/2002 | Knowlton |
| 6,485,486 B1 | 11/2002 | Trembly et al. |
| 6,496,737 B2 | 12/2002 | Rudie et al. |
| 6,496,738 B2 | 12/2002 | Carr |
| 6,514,249 B1 | 2/2003 | Maguire et al. |
| 6,527,753 B2 | 3/2003 | Sekine et al. |
| 6,547,788 B1 | 4/2003 | Maguire et al. |
| 6,575,969 B1 | 6/2003 | Rittman, III et al. |
| 6,599,288 B2 | 7/2003 | Maguire et al. |
| 6,629,951 B2 | 10/2003 | Laufer et al. |
| 6,629,974 B2 | 10/2003 | Penny et al. |
| 6,635,055 B1 | 10/2003 | Cronin |
| 6,645,234 B2 | 11/2003 | Evans et al. |
| 6,652,515 B1 | 11/2003 | Maguire et al. |
| 6,676,657 B2 | 1/2004 | Wood |
| D487,039 S | 2/2004 | Webster et al. |
| 6,689,127 B1 | 2/2004 | Gough et al. |
| 6,706,040 B2 | 3/2004 | Mahon et al. |
| 6,723,091 B2 | 4/2004 | Goble et al. |
| 6,740,108 B1 | 5/2004 | Just et al. |
| 6,770,070 B1 | 8/2004 | Balbierz |
| 6,773,409 B2 | 8/2004 | Truckai et al. |
| 6,780,183 B2 | 8/2004 | Jimenez, Jr. et al. |
| 6,786,905 B2 | 9/2004 | Swanson et al. |
| D496,997 S | 10/2004 | Dycus et al. |
| D499,181 S | 11/2004 | Dycus et al. |
| 6,869,431 B2 | 3/2005 | Maguire et al. |
| 6,893,436 B2 | 5/2005 | Woodard et al. |
| 6,898,454 B2 | 5/2005 | Atalar et al. |
| 6,932,776 B2 | 8/2005 | Carr |
| 6,997,925 B2 | 2/2006 | Maguire et al. |
| 7,004,938 B2 | 2/2006 | Ormsby et al. |
| 7,047,063 B2 | 5/2006 | Burbank et al. |
| 7,047,068 B2 | 5/2006 | Haissaguerre |
| D525,361 S | 7/2006 | Hushka |
| 7,089,063 B2 | 8/2006 | Lesh et al. |
| 7,113,832 B2 | 9/2006 | Longo |
| D531,311 S | 10/2006 | Guerra et al. |
| D533,942 S | 12/2006 | Kerr et al. |
| D535,027 S | 1/2007 | James et al. |
| 7,179,255 B2 | 2/2007 | Lettice et al. |
| 7,197,356 B2 | 3/2007 | Carr |
| D541,418 S | 4/2007 | Schechter et al. |
| 7,200,445 B1 | 4/2007 | Dalbec et al. |
| D541,938 S | 5/2007 | Kerr et al. |
| 7,233,820 B2 | 6/2007 | Gilboa |
| 7,261,001 B2 | 8/2007 | Heijnsdijk et al. |
| 7,263,398 B2 | 8/2007 | Carr |
| 7,285,116 B2 | 10/2007 | de la Rama et al. |
| 7,294,125 B2 | 11/2007 | Phalen et al. |
| 7,294,127 B2 | 11/2007 | Leung et al. |
| 7,300,436 B2 | 11/2007 | Penny et al. |
| 7,303,558 B2 | 12/2007 | Swanson |
| 7,318,823 B2 | 1/2008 | Sharps et al. |
| D564,662 S | 3/2008 | Moses et al. |
| 7,387,626 B2 | 6/2008 | Edwards et al. |
| 7,402,168 B2 | 7/2008 | Sanderson et al. |
| 7,410,486 B2 | 8/2008 | Fuimaono et al. |
| D576,932 S | 9/2008 | Strehler |
| 7,467,015 B2 | 12/2008 | van der Weide |
| 7,507,229 B2 | 3/2009 | Hewitt et al. |
| D594,736 S | 6/2009 | Esjunin |
| D594,737 S | 6/2009 | Kelly et al. |
| 7,559,916 B2 | 7/2009 | Smith et al. |
| 7,608,056 B2 | 10/2009 | Kennedy, II |
| 7,611,508 B2 | 11/2009 | Yang et al. |
| D606,203 S | 12/2009 | Husheer et al. |
| D613,412 S | 4/2010 | DeCarlo |
| 7,713,259 B2 | 5/2010 | Gosiengfiao et al. |
| 7,734,330 B2 | 6/2010 | Carr |
| 7,769,469 B2 | 8/2010 | Carr et al. |
| 7,771,425 B2 | 8/2010 | Dycus et al. |
| 7,783,336 B2 | 8/2010 | Macfarlane et al. |
| 7,850,685 B2 | 12/2010 | Kunis et al. |
| 7,871,406 B2 | 1/2011 | Nields et al. |
| 7,879,031 B2 | 2/2011 | Peterson |
| 7,879,033 B2 | 2/2011 | Sartor et al. |
| D634,010 S | 3/2011 | DeCarlo |
| 7,921,855 B2 | 4/2011 | Danek et al. |
| 7,933,660 B2 | 4/2011 | Carr |
| 7,993,351 B2 | 8/2011 | Worley et al. |
| 8,027,712 B2 | 9/2011 | Sioshansi et al. |
| 8,152,795 B2 | 4/2012 | Farr et al. |
| 8,155,416 B2 | 4/2012 | Nields et al. |

(56) References Cited

U.S. PATENT DOCUMENTS

| | | |
|---|---|---|
| 8,181,995 B2 | 5/2012 | DeCarlo |
| 8,182,466 B2 | 5/2012 | Stehr et al. |
| 8,224,424 B2 | 7/2012 | Burbank et al. |
| 8,226,566 B2 | 7/2012 | Nita |
| 8,251,987 B2 | 8/2012 | Willyard |
| 8,280,486 B2 | 10/2012 | Miller et al. |
| 8,287,463 B2 | 10/2012 | Field et al. |
| 8,289,551 B2 | 10/2012 | Wu |
| 8,292,881 B2 | 10/2012 | Brannan et al. |
| 8,303,581 B2 | 11/2012 | Arts et al. |
| 8,306,602 B2 | 11/2012 | Sirimanne et al. |
| 8,340,740 B2 | 12/2012 | Holzer et al. |
| D681,810 S | 5/2013 | DeCarlo |
| 8,476,242 B2 | 7/2013 | Mon |
| 8,480,665 B2 | 7/2013 | DeCarlo |
| 8,494,246 B2 | 7/2013 | Trumer et al. |
| 8,545,496 B2 | 10/2013 | Arts et al. |
| 8,597,291 B2 | 12/2013 | Arts et al. |
| 8,632,461 B2 | 1/2014 | Glossop |
| 8,655,454 B2 | 2/2014 | Prakash et al. |
| 8,768,485 B2 | 7/2014 | Hancock et al. |
| 8,795,268 B2 | 8/2014 | Willyard |
| 8,852,180 B2 | 10/2014 | Brannan |
| 8,892,185 B2 | 11/2014 | Chi Sing et al. |
| 8,906,008 B2 | 12/2014 | Brannan et al. |
| 8,920,410 B2 | 12/2014 | Brannan |
| 8,945,113 B2 | 2/2015 | Brannan et al. |
| 8,951,225 B2 | 2/2015 | Evard et al. |
| 8,968,290 B2 | 3/2015 | Brannan et al. |
| 8,968,300 B2 | 3/2015 | Brannan |
| 9,017,328 B2 | 4/2015 | Bahney |
| 9,044,254 B2 | 6/2015 | Ladtkow et al. |
| 9,066,681 B2 | 6/2015 | Arts et al. |
| 9,119,650 B2 | 9/2015 | Brannan et al. |
| 9,161,814 B2 | 10/2015 | Brannan et al. |
| 9,168,178 B2 | 10/2015 | Reid, Jr. et al. |
| 9,192,308 B2 | 11/2015 | Brannan et al. |
| 9,192,426 B2 | 11/2015 | Brannan et al. |
| 9,192,439 B2 | 11/2015 | Dunning et al. |
| 9,192,440 B2 | 11/2015 | Rossetto |
| 9,247,992 B2 | 2/2016 | Ladtkow et al. |
| 9,247,993 B2 | 2/2016 | Ladtkow et al. |
| 9,259,269 B2 | 2/2016 | Ladtkow et al. |
| 9,301,723 B2 | 4/2016 | Brannan et al. |
| 9,332,959 B2 | 5/2016 | Arts et al. |
| 9,358,067 B2 | 6/2016 | Lee et al. |
| 9,364,278 B2 | 6/2016 | DeCarlo et al. |
| 9,370,392 B2 | 6/2016 | Sharonov |
| 9,370,398 B2 | 6/2016 | Ladtkow et al. |
| 9,375,196 B2 | 6/2016 | Zheng et al. |
| 9,375,283 B2 | 6/2016 | Arts et al. |
| 9,439,712 B2 | 9/2016 | Sharonov |
| 9,498,286 B2 | 11/2016 | Brannan et al. |
| 9,504,524 B2 | 11/2016 | Behnke, II |
| 9,522,033 B2 | 12/2016 | Brannan |
| 9,526,568 B2 | 12/2016 | Ohri et al. |
| 9,549,757 B2 | 1/2017 | Arts et al. |
| 2001/0056289 A1 | 12/2001 | Sippensgroenewegen |
| 2002/0022835 A1 | 2/2002 | Lee |
| 2002/0022836 A1 | 2/2002 | Goble et al. |
| 2002/0026187 A1 | 2/2002 | Swanson |
| 2002/0040185 A1 | 4/2002 | Atalar et al. |
| 2002/0042564 A1 | 4/2002 | Cooper et al. |
| 2002/0049370 A1 | 4/2002 | Laufer et al. |
| 2003/0028095 A1 | 2/2003 | Tulley et al. |
| 2003/0060813 A1 | 3/2003 | Loeb et al. |
| 2003/0191451 A1 | 10/2003 | Gilmartin |
| 2003/0212394 A1 | 11/2003 | Pearson et al. |
| 2004/0030262 A1 | 2/2004 | Fisher et al. |
| 2004/0049254 A1 | 3/2004 | Longo |
| 2004/0073238 A1 | 4/2004 | Makower |
| 2004/0082860 A1 | 4/2004 | Haissaguerre |
| 2004/0097805 A1 | 5/2004 | Verard et al. |
| 2004/0133254 A1 | 7/2004 | Sterzer et al. |
| 2004/0176740 A1 | 9/2004 | Chouinard |
| 2005/0015081 A1 | 1/2005 | Turovskiy et al. |
| 2005/0043713 A1 | 2/2005 | Zhou |
| 2005/0080333 A1 | 4/2005 | Piron et al. |
| 2005/0080334 A1 | 4/2005 | Willis |
| 2005/0096502 A1 | 5/2005 | Khalili |
| 2005/0113640 A1 | 5/2005 | Saadat et al. |
| 2005/0215942 A1 | 9/2005 | Abrahamson et al. |
| 2005/0245919 A1 | 11/2005 | van der Welde |
| 2005/0245920 A1 | 11/2005 | Vitullo et al. |
| 2005/0273006 A1 | 12/2005 | Stewart et al. |
| 2006/0004351 A1 | 1/2006 | Arless et al. |
| 2006/0009833 A1 | 1/2006 | Chobotov et al. |
| 2006/0089637 A1 | 4/2006 | Werneth et al. |
| 2006/0100614 A1 | 5/2006 | Long |
| 2006/0155270 A1 | 7/2006 | Hancock et al. |
| 2006/0167416 A1 | 7/2006 | Mathis et al. |
| 2006/0173280 A1 | 8/2006 | Goosen et al. |
| 2006/0241564 A1 | 10/2006 | Corcoran et al. |
| 2006/0253102 A1 | 11/2006 | Nance et al. |
| 2006/0253126 A1 | 11/2006 | Bjerken et al. |
| 2006/0258955 A1 | 11/2006 | Hoffman et al. |
| 2007/0027385 A1 | 2/2007 | Brister et al. |
| 2007/0032723 A1 | 2/2007 | Glossop |
| 2007/0060944 A1 | 3/2007 | Boldenow et al. |
| 2007/0077230 A1 | 4/2007 | Mon |
| 2007/0088319 A1 | 4/2007 | Martone |
| 2007/0129717 A1 | 6/2007 | Brown et al. |
| 2007/0185554 A1 | 8/2007 | Appling et al. |
| 2007/0208301 A1 | 9/2007 | Evard et al. |
| 2007/0282319 A1 | 12/2007 | van der Weide et al. |
| 2007/0287912 A1 | 12/2007 | Khuri-Yakub et al. |
| 2007/0299353 A1 | 12/2007 | Harlev et al. |
| 2008/0033286 A1 | 2/2008 | Whitmore et al. |
| 2008/0033424 A1 | 2/2008 | van der Weide et al. |
| 2008/0091169 A1 | 4/2008 | Heideman et al. |
| 2008/0147056 A1 | 6/2008 | van der Weide et al. |
| 2008/0208031 A1 | 8/2008 | Kurpad et al. |
| 2008/0208039 A1 | 8/2008 | Kurpad et al. |
| 2008/0228167 A1 | 9/2008 | Mittermeyer et al. |
| 2008/0255507 A1 | 10/2008 | Mushtaha |
| 2008/0262342 A1 | 10/2008 | Averbruch |
| 2008/0262472 A1 | 10/2008 | Lunn et al. |
| 2008/0269601 A1 | 10/2008 | Schwamb |
| 2009/0018403 A1 | 1/2009 | Black et al. |
| 2009/0076409 A1 | 3/2009 | Wu et al. |
| 2009/0076498 A1 | 3/2009 | Saadat et al. |
| 2009/0080604 A1 | 3/2009 | Shores et al. |
| 2009/0187180 A1 | 7/2009 | Brannan |
| 2009/0216115 A1 | 8/2009 | Seiler et al. |
| 2009/0222002 A1 | 9/2009 | Bonn et al. |
| 2009/0234220 A1 | 9/2009 | Maschke |
| 2009/0259105 A1 | 10/2009 | Miyano et al. |
| 2009/0295674 A1 | 12/2009 | Bonn |
| 2009/0312754 A1 | 12/2009 | Lenihan et al. |
| 2010/0004631 A1 | 1/2010 | Zhou |
| 2010/0036369 A1 | 2/2010 | Hancock |
| 2010/0053015 A1 | 3/2010 | Willyard |
| 2010/0076424 A1 | 3/2010 | Carr |
| 2010/0121319 A1 | 5/2010 | Chu et al. |
| 2010/0160719 A1 | 6/2010 | Kassab et al. |
| 2010/0185191 A1 | 7/2010 | Carr et al. |
| 2010/0234726 A1 | 9/2010 | Sirimanne et al. |
| 2010/0249754 A1 | 9/2010 | Griffin et al. |
| 2010/0256621 A1 | 10/2010 | Babkin et al. |
| 2010/0262134 A1 | 10/2010 | Jensen et al. |
| 2010/0268196 A1 | 10/2010 | Hastings et al. |
| 2010/0305559 A1 | 12/2010 | Brannan et al. |
| 2010/0312096 A1 | 12/2010 | Guttman et al. |
| 2011/0004205 A1 | 1/2011 | Chu et al. |
| 2011/0009895 A1 | 1/2011 | Gertner |
| 2011/0029049 A1 | 2/2011 | Vertikov et al. |
| 2011/0034913 A1 | 2/2011 | Brannan |
| 2011/0034917 A1 | 2/2011 | Brannan |
| 2011/0040300 A1 | 2/2011 | Brannan |
| 2011/0046622 A1 | 2/2011 | McAuley |
| 2011/0054458 A1 | 3/2011 | Behnke |
| 2011/0060326 A1 | 3/2011 | Smith et al. |
| 2011/0077634 A1 | 3/2011 | Brannan |
| 2011/0077635 A1 | 3/2011 | Bonn |

(56) References Cited

U.S. PATENT DOCUMENTS

| | | |
|---|---|---|
| 2011/0077638 A1 | 3/2011 | Brannan |
| 2011/0085720 A1 | 4/2011 | Barak et al. |
| 2011/0118721 A1 | 5/2011 | Brannan |
| 2011/0118723 A1 | 5/2011 | Turner et al. |
| 2011/0130750 A1 | 6/2011 | Ormsby et al. |
| 2011/0166518 A1 | 7/2011 | Nguyen et al. |
| 2011/0166519 A1 | 7/2011 | Nguyen et al. |
| 2011/0200171 A1 | 8/2011 | Beetel et al. |
| 2011/0238083 A1 | 9/2011 | Moll et al. |
| 2011/0282336 A1 | 11/2011 | Brannan et al. |
| 2011/0301587 A1 | 12/2011 | Deem et al. |
| 2011/0319880 A1 | 12/2011 | Prakash et al. |
| 2012/0029359 A1 | 2/2012 | Sterzer et al. |
| 2012/0029503 A1 | 2/2012 | Bonn |
| 2012/0035603 A1 | 2/2012 | Lenihan |
| 2012/0065481 A1 | 3/2012 | Hunter et al. |
| 2012/0071822 A1 | 3/2012 | Romo et al. |
| 2012/0078175 A1 | 3/2012 | Vreeman |
| 2012/0078230 A1 | 3/2012 | Lowe et al. |
| 2012/0101370 A1 | 4/2012 | Razzaque et al. |
| 2012/0172680 A1 | 7/2012 | Gelfand et al. |
| 2012/0172860 A1 | 7/2012 | Brannan |
| 2012/0259326 A1* | 10/2012 | Brannan .......... A61B 17/00234 606/33 |
| 2012/0277730 A1 | 11/2012 | Salahieh et al. |
| 2013/0090552 A1 | 4/2013 | Ramamurthy et al. |
| 2013/0116679 A1 | 5/2013 | Van der Weide et al. |
| 2013/0137977 A1 | 5/2013 | Eder |
| 2013/0197481 A1 | 8/2013 | Guo et al. |
| 2013/0197482 A1 | 8/2013 | Akitomo |
| 2013/0225942 A1 | 8/2013 | Holsing et al. |
| 2013/0225943 A1 | 8/2013 | Holsing et al. |
| 2013/0225973 A1 | 8/2013 | Gertner |
| 2013/0225994 A1 | 8/2013 | Hsu et al. |
| 2013/0231556 A1 | 9/2013 | Holsing et al. |
| 2013/0261617 A1 | 10/2013 | Podhajsky |
| 2013/0310823 A1 | 11/2013 | Gelfand et al. |
| 2013/0317495 A1 | 11/2013 | Brannan |
| 2013/0324910 A1 | 12/2013 | Ohri et al. |
| 2013/0324911 A1 | 12/2013 | Ohri et al. |
| 2013/0338477 A1 | 12/2013 | Glossop et al. |
| 2013/0345541 A1 | 12/2013 | Nau, Jr. |
| 2013/0345552 A1 | 12/2013 | Arts et al. |
| 2014/0005657 A1 | 1/2014 | Brannan et al. |
| 2014/0018793 A1 | 1/2014 | Sharonov |
| 2014/0024909 A1 | 1/2014 | Vij et al. |
| 2014/0066922 A1 | 3/2014 | Coe et al. |
| 2014/0094789 A1 | 4/2014 | Brannan |
| 2014/0094793 A1 | 4/2014 | Sharonov |
| 2014/0094794 A1 | 4/2014 | Orszulak |
| 2014/0296875 A1 | 10/2014 | Moll et al. |
| 2015/0141985 A1 | 5/2015 | Mayse et al. |

FOREIGN PATENT DOCUMENTS

| | | |
|---|---|---|
| CN | 1103807 C | 3/2003 |
| CN | 1489807 A | 4/2004 |
| CN | 101589458 A | 11/2009 |
| CN | 102711643 A | 10/2012 |
| CN | 102802548 A | 11/2012 |
| CN | 202568444 U | 12/2012 |
| CN | 102846376 A | 1/2013 |
| CN | 102883659 A | 1/2013 |
| CN | 103841913 A | 6/2014 |
| CN | 104042340 A | 9/2014 |
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 246350 A1 | 11/1987 |
| EP | 0521264 A2 | 1/1993 |
| EP | 556705 A1 | 8/1993 |
| EP | 0558429 A1 | 9/1993 |
| EP | 0648515 A1 | 4/1995 |
| EP | 836868 A2 | 4/1998 |
| EP | 882955 A1 | 12/1998 |
| EP | 1034747 A1 | 9/2000 |
| EP | 1034748 A1 | 9/2000 |
| EP | 1055400 A1 | 11/2000 |
| EP | 1159926 A3 | 3/2003 |
| EP | 2147651 A1 | 1/2010 |
| EP | 2322113 A1 | 5/2011 |
| EP | 2371314 A2 | 10/2011 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 55106 | 1/1993 |
| JP | 0540112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 20018944 | 1/2001 |
| JP | 2001003776 A | 1/2001 |
| JP | 200129356 | 2/2001 |
| JP | 200137775 A | 2/2001 |
| JP | 2001128990 A | 5/2001 |
| JP | 2001231870 A | 8/2001 |
| JP | 2001518351 A | 10/2001 |
| JP | 2008142467 A | 6/2008 |

(56) References Cited

FOREIGN PATENT DOCUMENTS

| | | |
|---|---|---|
| JP | 2011516184 A | 5/2011 |
| JP | 2012187405 A | 10/2012 |
| KR | 20070093068 A | 9/2007 |
| KR | 20100014406 A | 2/2010 |
| KR | 20120055063 A | 5/2012 |
| SU | 166452 | 1/1965 |
| SU | 401367 A1 | 10/1973 |
| SU | 727201 A2 | 4/1980 |
| WO | 9416632 A1 | 8/1994 |
| WO | 9724074 A1 | 7/1997 |
| WO | 0010456 A1 | 3/2000 |
| WO | 0036985 A2 | 6/2000 |
| WO | 0057811 A1 | 10/2000 |
| WO | 0100114 A1 | 1/2001 |
| WO | 0167035 A1 | 9/2001 |
| WO | 0245790 A2 | 6/2002 |
| WO | 2006084676 A1 | 8/2006 |
| WO | 2008068485 A2 | 6/2008 |
| WO | 2010035831 A1 | 4/2010 |
| WO | 2011063061 A2 | 5/2011 |
| WO | 2011139589 A2 | 11/2011 |
| WO | 2011140087 A2 | 11/2011 |
| WO | 2012071388 A2 | 5/2012 |
| WO | 2013192553 A1 | 12/2013 |
| WO | 2014025551 A1 | 2/2014 |

OTHER PUBLICATIONS

B. F. Mullan et al., (May 1999) "Lung Nodules: Improved Wire for CT-Guided Localization," Radiology 211:561-565.

Chung et al., "Clinical Experience of Sutureless Closed Hemontoidectomy with LigaSureTM " Diseases of the Colon & Rectum, vol. 46, No. 1, Jan. 2003.

E. David Crawford, "Use of a Novel Vessel Sealing Technology in Management of the Dorsal Veinous Complex" Sales/Product Literature 2000.

Esterline, "Light Key Projection Keyboard" Advanced Input Systems, located at: <http://www.advanced-input.com/lightkey> 2002.

Geddes et al., "The Measurement of Physiologic Events by Electrical Impedence" Am. J. MI, Jan. Mar. 1964, pp. 16-27.

Goldberg et al., "Image-guided Radiofrequency Tumor Ablation: Challenges and Opportunities—Part I", (2001) J Vasc. Interv. Radiol, vol. 12, pp. 1021-1032.

Goldberg et al. (1995) "Saline-enhanced RF Ablation: Demonstration of Efficacy and Optimization of Parameters", Radiology, 197(P): 140 (Abstr).

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.

Herman at al., "Laparoscopic Intestinal Resection With the LigaSureTM Vessel Sealing System: A Case Report" Innovations That Work, Feb. 2002.

Humphries Jr. et al., "Finite-Element Codes to Model Electrical Heating and Non-LInear Thermal Transport in Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSureTM Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSureTM Vessel Sealing System in Hemorrhoidectormy" American College of Surgeons (ACS) Clinic La Congress Poster (2000).

Johnson et al., "New Low-Profile Applicators for Local Heating of Tissues", IEEE Transactions on Biomedical Engineering, vol. BME-31, No. 1, Jan. 1984, pp. 28-37.

Johnson, "Use of the LigaSureTM Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSureTM System Used in Laparoscopic 1st and 2nd Stage Orchiopexy" Innovations That Work, Nov. 2002.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

Anonymous. (1987) Homer Mammalok.TM. Breast Lesion NeedlelWire Localizer, Namic .RTM. Angiographic Systems . Division, Glens Falls, New York, (Hospital products price list), 4 pages.

T.Seki et al., (1994) "Ultrasonically Guided Percutaneous Microwave Coagulation Therapy for Small Hepatocellular Carcinoma," Cancer 74(3):817-825.

Carbonell et al., "Comparison of the Gyms PlasmaKinetic Sealer and the Valleylab LigaSure.TM. Device in the Hemostasis of Small, Medium, and Large-Sized Arteries" Carolinas Laparoscopic and Advanced Surgery Program, Carolinas MedicalCenter,Chartotte, NC 2003.

Ni Wei et al., "A Signal Processing Method for the Coriolis Mass Flowmeter Based on a Normalized . . . " Journal of Applied Sciences-Yingyong Kexue Xuebao, Shangha CN, vol. 23, No. 2:(Mar. 2005); pp. 160-184.

B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.

B. Levy M.D. et al., "Update on Hysterectomy New Technologies and Techniques" OBG Management, Feb. 2003.

B. Levy M.D., "Use of a New Vessel Ligation Device During Vaginal Hysterectomy" FIGO 2000, Washington, D.C.

B. T. Heniford M.D. et al., "Initial Research and Clinical Results with an Electrothermal Bipolar Vessel Sealer" Oct. 1999.

Bergdahl et al., "Studies on Coagulation and the Development of an Automatic Computerized Bipolar Coagulator" Journal of Neurosurgery 75:1 (Jul. 1991), pp. 148-151.

Bulletin of the American Physical Society, vol. 47, No. 5, Aug. 2002, p. 41.

C. F. Gottlieb et al., "Interstitial Microwave Hyperthermia Applicators having Submillimetre Diameters", Int. J. Hyperthermia, vol. 6, No. 3, pp. 707-714, 1990.

C. H. Durney et al., "Antennas for Medical Applications", Antenna Handbook: Theory Application and Design, p. 24-40, Van Nostrand Reinhold, 1988 New York, V.T. Lo, S.W. Lee.

Carus et al., "Initial Experience With the LigaSure.TM. Vessel Sealing System in Abdominal Surgery" Innovations That Work, Jun. 2002.

Chicharo et al., "A Sliding Goertzel Algorithm" Aug. 1996 DOS pp. 283-297 Signal Processing, Elsevier Science Publishers B.V. Amsterdam, NL, vol. 52, No. 3.

Chou, C.K., (1995) "Radiofrequency Hyperthermia in Cancer Therapy," Chapter 94ln Biologic Effects of Nonionizing Electromagnetic Fields, CRC Press, Inc., pp. 1424-1428.

Cosman et al., "Methods of Making Nervous System Lesions" In William RH, Rengachary SS (eds): Neurosurgery, New York: McGraw-Hill, vol. 111, (1984), pp. 2490-2499.

Cosman et al., "Radiofrequency Lesion Generation and its Effect on Tissue Impedence", Applied Neurophysiology, 51:230-242, 1988.

Cosman et al., "Theoretical Aspects of Radiofrequency Lesions in the Dorsal Root Entry Zone" Neurosurgery 15: (1984), pp. 945-950.

(56) References Cited

OTHER PUBLICATIONS

Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
Esterline Product Literature, "Light Key: Visualize a Virtual Keyboard. One With No Moving Parts", Nov. 1, 2003; 4 pages.
Notification of the First Office Action issued by the State Intellectual Property Office of the People's Republic of China dated Jan. 28, 2019 in corresponding Chinese Patent Application No. 201710109752.5, with English translation.
LigaSureTM Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W, "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'L Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
Urologix, Inc.—Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.

(56) References Cited

OTHER PUBLICATIONS

Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.

* cited by examiner

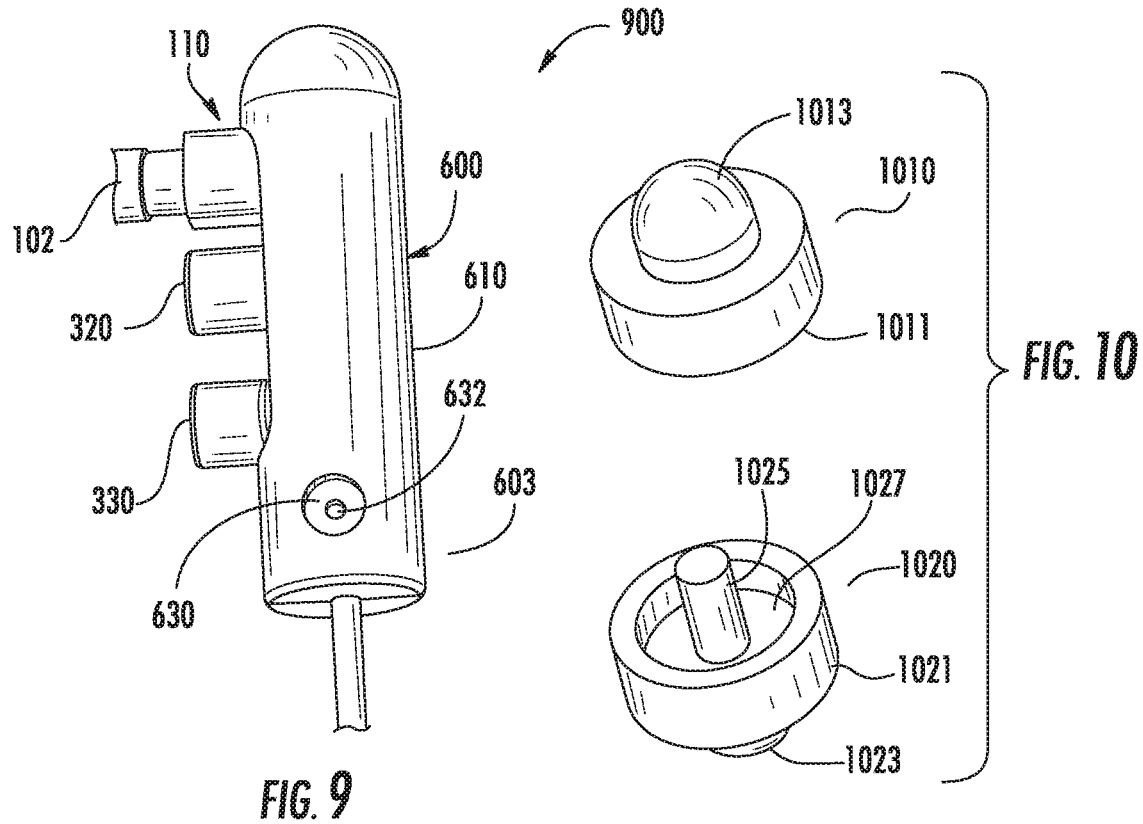
FIG. 9
FIG. 10
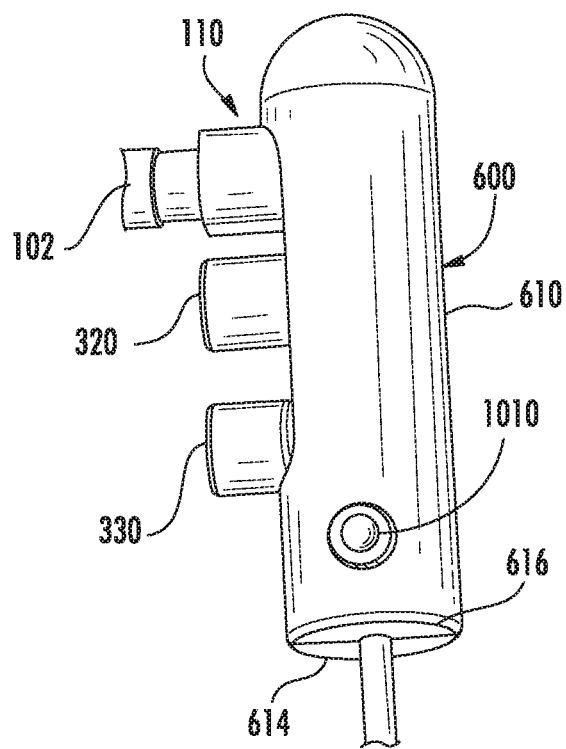
FIG. 11

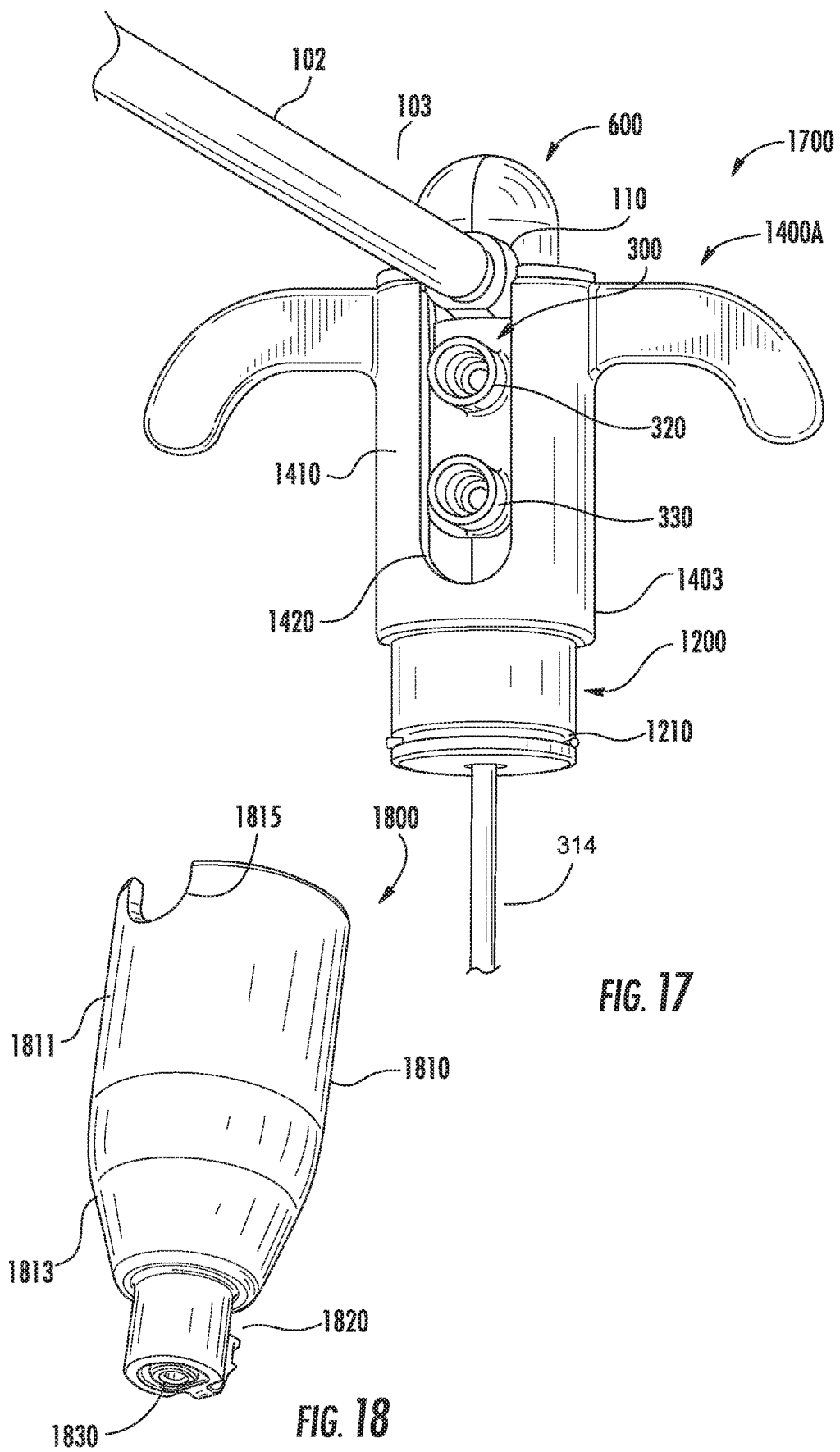

90-DEGREE INTERLOCKING GEOMETRY FOR INTRODUCER FOR FACILITATING DEPLOYMENT OF MICROWAVE RADIATING CATHETER

The present application claims the benefit of and priority to U.S. Provisional Application Ser. No. 62/301,255, filed on Feb. 29, 2016, the entire contents of which are incorporated herein by reference.

BACKGROUND

1. Technical Field

The present disclosure relates generally to microwave catheters, and, more particularly, to a 90-degree interlocking geometry for an introducer used to facilitate deployment of a microwave radiating catheter.

2. Discussion of Related Art

Electromagnetic fields can be used to heat and destroy tumor cells. Treatment may involve inserting ablation probes into tissues where cancerous tumors have been identified. Once the ablation probes are properly positioned, the ablation probes induce electromagnetic fields within the tissue surrounding the ablation probes.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic fields to heat or ablate tissue.

Devices utilizing electromagnetic fields have been developed for a variety of uses and applications. Typically, apparatuses for use in ablation procedures include a power generation source, e.g., a microwave generator that functions as an energy source and a surgical instrument (e.g., microwave ablation probe having an antenna assembly) for directing energy to the target tissue. The generator and surgical instrument are typically operatively coupled by a cable assembly having a plurality of conductors for transmitting energy from the generator to the instrument, and for communicating control, feedback, and identification signals between the instrument and the generator.

There are several types of microwave probes in use, e.g., monopole, dipole, and helical, which may be used in tissue ablation applications. The heating of tissue for thermal ablation is accomplished through a variety of approaches, including conduction of heat from an applied surface or element, ionic agitation by electrical current flowing from an electrode to a ground pad (current-based technology), optical wavelength absorption, or, in the case of microwave ablation, by dielectric relaxation of water molecules within an antenna electromagnetic field (field-based technology).

Because of the various components needed in a microwave ablation assembly, the weight of the microwave ablation assembly is increased, thus causing difficultly in handling of such assembly. The weight of the microwave ablation assembly may limit the surgeon's capability of using surgical tools simultaneously with the microwave ablation assembly, as well as causing fatigue on the hands and arms of the surgeon when performing minimally-invasive procedures. Accordingly, there is a need for an apparatus that would facilitate one-handed actuation and manipulation of the catheter and surgical instrument leaving one hand to perform other tasks, as well as for an apparatus that would limit the number of steps required, as each step causes movement of the catheter within the patient.

SUMMARY

One aspect of the present disclosure is directed to a microwave ablation assembly including a first cannula, a trocar insertable through the first cannula and configured to facilitate insertion of the first cannula into a target tissue, and a microwave antenna assembly configured to interlock with the first cannula. The microwave antenna assembly includes a coaxial feedline having a radiating section formed thereon, the microwave antenna assembly configured to be inserted into the first cannula. The microwave ablation assembly further includes an actuator operatively connected to one of the first cannula or microwave antenna assembly, where operation of the actuator between a first position and a second position exposes the radiating section of the microwave antenna assembly from a distal portion of the first cannula.

The microwave ablation assembly may include a transition head adapted to connect the microwave antenna assembly to a microwave transmission cable assembly. Additionally the microwave ablation assembly may include a multi-lumen housing having a hub formed at a proximal end thereof, the hub defining a longitudinal axis there through, and including an inflow port and an outflow port to provide respective ingress and egress of a coolant to and from the multi-lumen housing for cooling the microwave antenna assembly.

The microwave ablation assembly may include a second cannula extending from the multi-lumen housing, in fluid communication with the inflow and outflow ports, and receiving the microwave antenna assembly, wherein coolant flows through the second cannula and over the microwave antenna assembly.

In accordance with a further aspect of the disclosure, the inflow port and the outflow port are parallel to each other, and perpendicular to the longitudinal axis defined by the hub. Further, the transition head may include a first section and a second section, the first section adapted to be coupled to a distal end of a microwave transmission cable assembly and the second section adapted to be coupled to a proximal end of the coaxial feed line. Still further, the microwave ablation assembly may include an o-ring adapted to fit on the second section of the transition head which is adapted to be received within the hub of the multi-lumen housing such that the o-ring forms a fluid tight seal between the second section of the transition head and the hub upon connection.

In accordance with a further aspect of the disclosure, the actuator defines a pair of recesses on opposed surfaces thereof, and an opening for exposing the inflow port, the outflow port, and the distal end of the cable assembly. Pins may be received in the pair of recesses on opposed surfaces of the actuator. Further, a locking spindle may be incorporated where the locking spindle is assembled over the actuator. The locking spindle may include a body portion defining a pair of longitudinal slots on opposed surfaces thereof, where the longitudinal slots each separate a first end from a second end.

In a further aspect of the disclosure, the actuator may include a sliding spindle which is configured to slide within the locking spindle such that the pins travel along the pair of longitudinal slots to lock between the first ends and the second ends. The actuator may include a control ring assembled over a portion of the locking spindle and the sliding spindle. The control ring may include a body portion, a pair of opposed projections extending from the body portion, and a pair of opposed elongated camming surfaces configured and dimensioned to receive the pins and guide longitudinal movement thereof.

A nose cone may be assembled over a portion of the control ring, the nose cone having a proximal end and a distal end, the distal end having a tip portion with a locking mechanism, and the proximal end defining a cut-out portion configured to receive the outflow port there through. The locking spindle may include a retaining ring configured to secure the nose cone to the locking spindle. A housing formed on a proximal region of the first cannula may be configured to mate with the locking mechanism of the nose cone.

In accordance with aspects of the present disclosure, upon actuation of the actuator the sliding spindle and second cannula remain stationary and the first cannula is drawn in the direction of the sliding spindle to expose the second cannula and the radiating section of the microwave antenna assembly located therein. Additionally or alternatively, the locking spindle, the control ring, and the nose cone may be drawn in the direction of the sliding spindle to expose the second cannula and the radiating section of the microwave antenna assembly located therein.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 9 is an enlarged view of the sliding spindle of FIG. 6 depicting a recess for receiving a pin, in accordance with aspects of the present disclosure;

FIG. 10 is a perspective view of a pair of pins inserted into recesses of the sliding spindle of FIG. 6, in accordance with aspects of the present disclosure;

FIG. 11 is an enlarged view of the sliding spindle of FIG. 6 depicting the pair of pins of FIG. 10 inserted thereto, in accordance with aspects of the present disclosure;

FIG. 17 is an enlarged view of the control ring assembled onto the locking spindle, the locking spindle assembled onto the sliding spindle, and the sliding spindle assembled onto the microwave transmission and radiation component, and depicting the inflow and outflow ports, in accordance with aspects of the present disclosure;

FIG. 18 is a perspective view of a nose cone, in accordance with aspects of the present disclosure;

DETAILED DESCRIPTION

Figure 1:
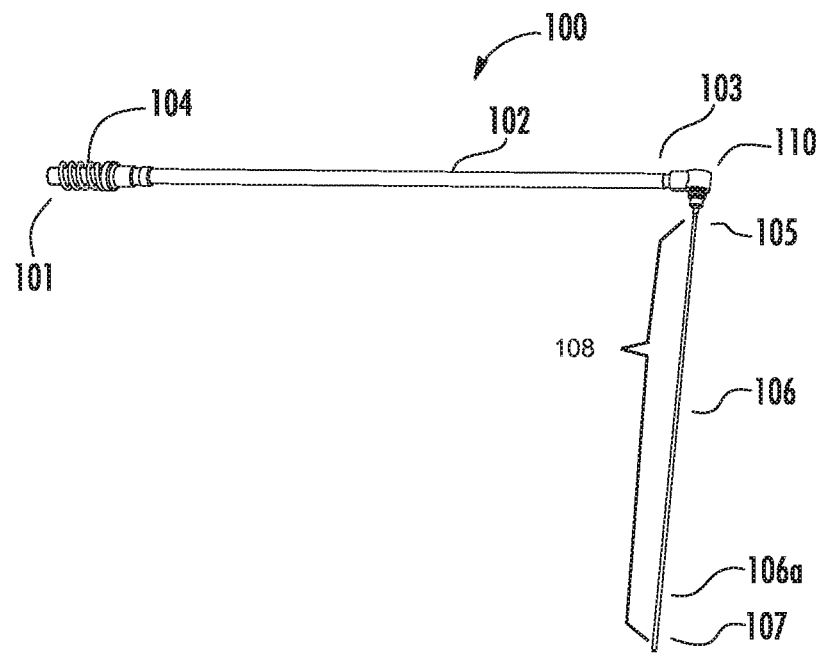
FIG. 1 is a perspective view of a microwave transmission and radiation component, in accordance with aspects of the present disclosure.

The present disclosure is directed to a microwave catheter connected to an access channel device at a 90-degree angle or in a substantially perpendicular configuration. The 90-degree transition geometry is enabled by the use of a 90-degree transition head, as well as a multi-lumen overmolded fluid hub having an inflow port and an outflow port that may be substantially parallel to each other. The 90-degree connection or 90-degree interlocking geometry between the microwave catheter and the access channel device reduces the load or pressure applied to the surgeon's hands and arms when manipulating such devices. Additionally, the 90-degree connection or 90-degree interlocking geometry between the microwave catheter and the access channel device enables quick separation of the cannula from the trocar so that the access channel device can be easily placed at a target location. Moreover, the 90-degree connection or 90-degree interlocking geometry between the microwave catheter and the access channel device enables needle-like placement of an elongated non-rigid microwave radiation catheter into targeted tissue for thermal ablation during open, laparoscopic or transcutaneous procedures without a guide wire or pre-established access path.

Embodiments of the microwave ablation systems and components are described with reference to the accompanying drawings. Like reference numerals may refer to similar or identical elements throughout the description of the figures. As shown in the drawings and as used in this description, the term "proximal" refers to that portion of the apparatus, or component of the apparatus, closer to the user and the term "distal" refers to that portion of the apparatus, or a component of the apparatus, farther from the user.

This description may use the phrases "in an embodiment," "in embodiments," "in some embodiments," or "in other embodiments," which may each refer to one or more of the same or different embodiments in accordance with the present disclosure.

As it is used in this description, "microwave" generally refers to electromagnetic waves in the frequency range of 300 megahertz (MHz) ($3\times10^8$ cycles/second) to 300 gigahertz (GHz) ($3\times10^{11}$ cycles/second). As it is used in this description, "ablation procedure" generally refers to any ablation procedure, such as, for example, microwave ablation, radiofrequency (RF) ablation, or microwave or RF ablation-assisted resection. As it is used in this description, "transmission line" generally refers to any transmission medium that can be used for the propagation of signals from one point to another. As it is used in this description, "fluid" generally refers to a liquid, a gas, or both. The term "coolant" may be used interchangeable with the term "fluid."

Reference will now be made in detail to embodiments of the present disclosure. While certain exemplary embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Referring initially to FIG. 1, the microwave transmission and radiation component 100 includes a microwave transmission cable assembly 102 connected to a microwave antenna assembly 108 via a transition head 110. The microwave antenna assembly 108 includes a feedline 106 and a radiating section 106a located at a distal portion thereof and in electrical communication with the coaxial feed line 106. The transition head 110 may be referred to as a 90-degree transition head 110. The microwave transmission cable assembly 102 has a proximal end 101 and a distal end 103. The proximal end 101 may have a spring-biased coupling element 104. The spring-biased coupling element 104 may be coupled to a housing 2212 (FIG. 22) for connection to a microwave generator. The microwave antenna assembly 108 has a proximal end 105 and a distal end 107. In some embodiments, the microwave transmission cable assembly 102 has a first diameter and the coaxial feed line 106 has a second diameter, the first diameter being greater than the second diameter. The transition head 110 allows for a 90-degree connection to be established between the microwave transmission cable assembly 102 and the coaxial feed line 106 of the microwave antenna assembly 108, as described in detail below with reference to FIG. 2.

Figure 2:
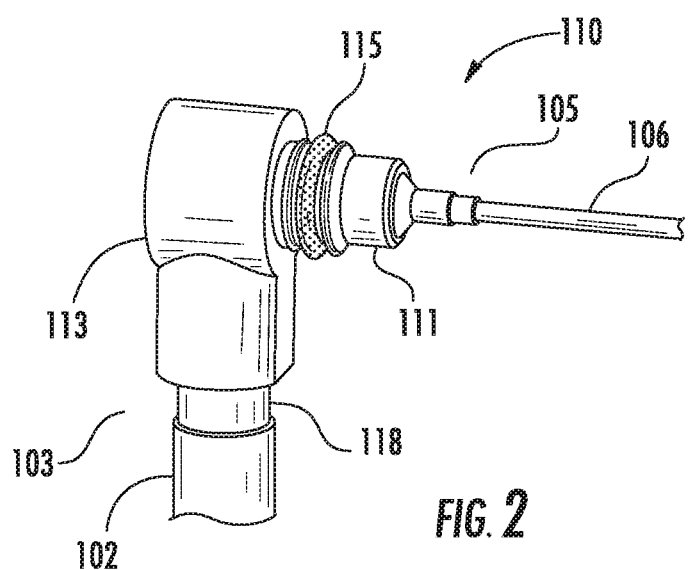
FIG. 2 is a perspective view of a transmission head of the microwave transmission and radiation component of FIG. 1, in accordance with aspects of the present disclosure.

As shown in FIG. 2, the transition head 110 is formed by a first section 111 and a second section 113. The first and second sections 111, 113 are perpendicular to each other and form a 90-degree angle therebetween. The first and second sections 111, 113 form a 90-degree interlocking geometry. The first section 111 is coupled to the proximal end 105 of the coaxial feed line 106. The second section 113 is coupled to the distal end 103 of the microwave transmission cable assembly 102 via a tubular member 118. A 90-degree coaxial cable connector (not shown but incorporated into the transition head 110) enables electrical connection between the microwave transmission cable assembly 102 and the coaxial feed line 106. The first section 111 further includes an o-ring 115 circumferentially positioned about a portion thereof. The o-ring 115 does not contact the second section 113, but ensures a water tight seal when the transition head 110 is integrated with a multi-lumen hub as described below with respect to FIG. 3.

Figure 3:
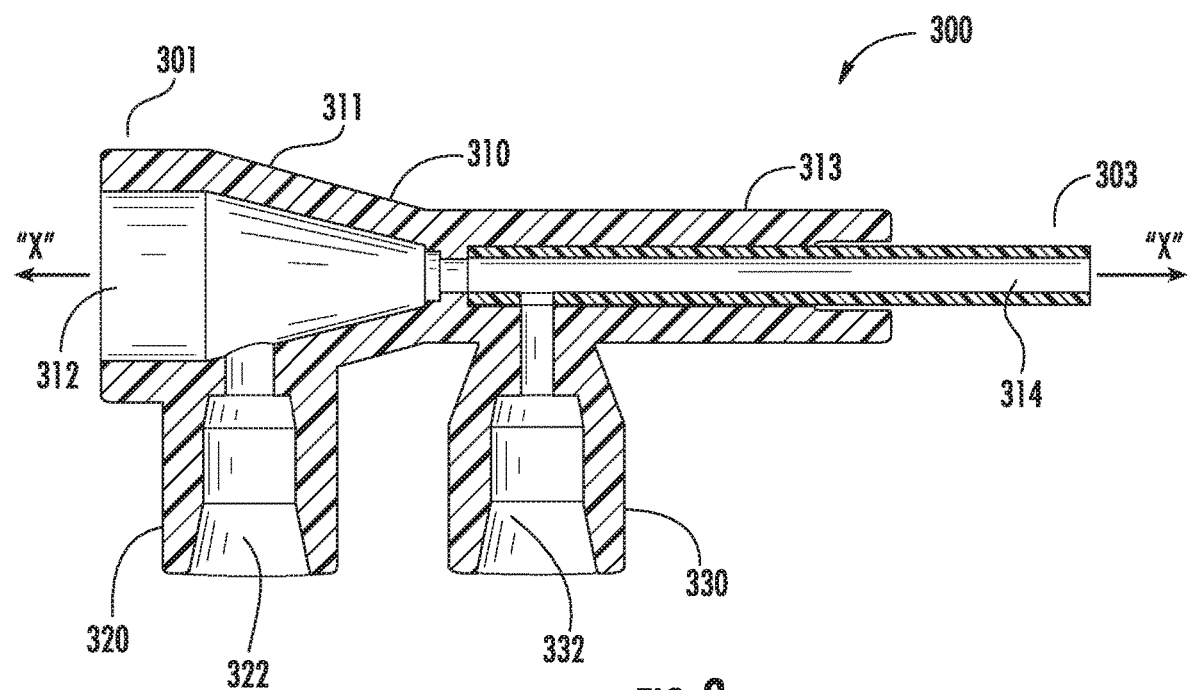
FIG. 3 is a cross-sectional view of a multi-lumen overmolded fluid hub, in accordance with aspects of the present disclosure.

As shown in FIG. 3, the multi-lumen hub 300 includes a body portion or hub 310. The body portion 310 has a proximal end 301 and a distal end 303. The body portion 310 defines an upper body portion 311 and a lower body portion 313. The upper body portion 311 defines a chamber 312 and the lower body portion 313 houses a cannula 314. The chamber 312 is in fluid communication with the cannula 314. The cannula 314 defines a longitudinal axis "X" therethrough.

The cannula 314 may be formed of a rigid or a flexible material. In certain embodiments a combination of rigid (e.g., steel or ceramic) and flexible (e.g., polymeric materials) may be employed. Further, the cannula 314 may be pre-curved or shaped to reach a desired location within the physiology of a patient. Still further, the cannula 314 may employ one or more pairs of steering wires, enabling the cannula to be articulated in one or more directions. The use of a flexible material enables the advancement and navigation of the cannula 314 for the proper placement of the radiating section 106a housed therein, as will be described herein below.

The multi-lumen hub 300 includes an inflow port 320 and an outflow port 330. The inflow port 320 may also be referred to as a fluid intake port and the outflow port 330 may also be referred to as a fluid return port. The inflow port 320 defines an inflow lumen 322 therethrough and the outflow port 330 defines an outflow lumen 332 therethrough. The inflow and outflow ports 320, 330 provide respective ingress and egress of a fluid or coolant to and from the body portion 310 of the multi-lumen hub 300 for cooling the coaxial feed line 106 and radiating section 106a of the microwave transmission and radiation component 100 of FIG. 1.

The inflow port 320 is substantially parallel to the outflow port 330. Thus, the inflow lumen 322 of the inflow port 320 is also substantially in parallel to the outflow lumen 332 of the outflow port 330. The inflow and outflow ports 320, 330 may be substantially perpendicular to the longitudinal axis "X" defined by the cannula 314. The inflow and outflow ports 320, 330 have substantially circular openings. However, one skilled in the art may contemplate various geometrical openings for inflow and outflow ports 320, 330. The inflow port 320 cooperates with the upper body portion 311 of the body portion 310, whereas the outflow port 330 cooperates with the lower body section 313 of the body portion 310. The inflow port 320 is in fluid communication with the chamber 312, whereas the outflow port 330 is in fluid communication with the cannula 314. The cannula 314 extends beyond a distal end of the lower body portion 313 of the body portion 310. The diameter of the inflow and outflow lumens 322, 332 are greater than the diameter of the cannula 314. The diameter of the chamber 312 is greater than the diameter of the inflow and outflow ports 320, 330.

Figure 4:
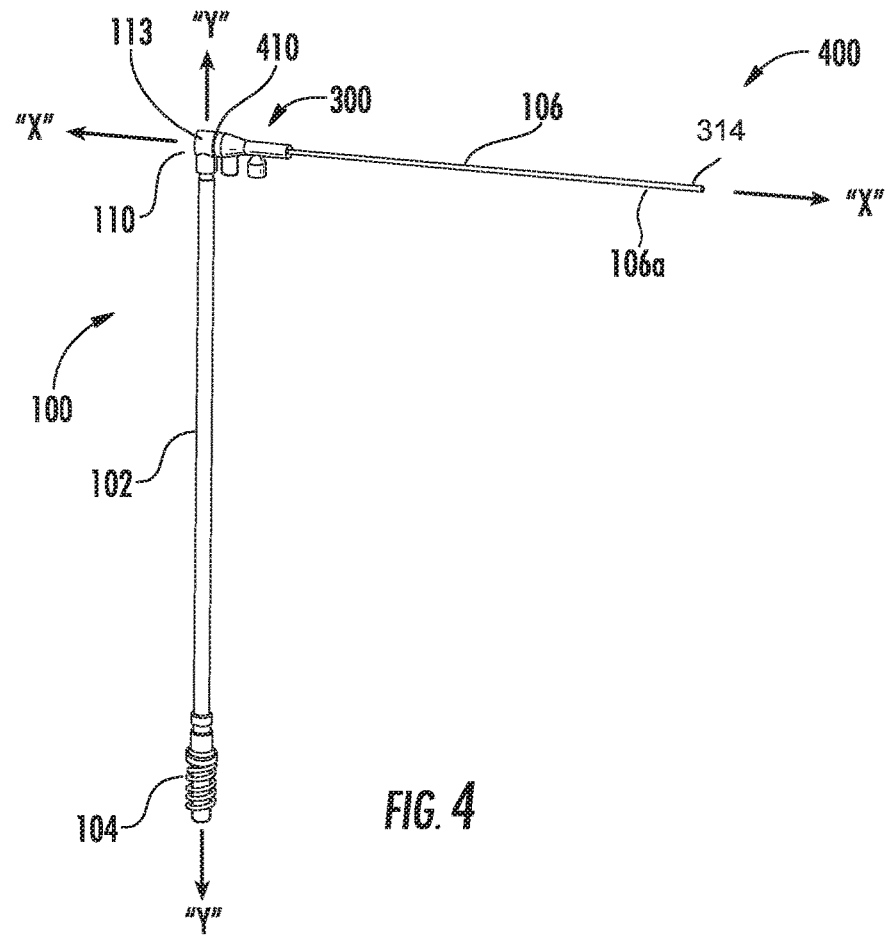
FIG. 4 is a perspective view of a coaxial feedline having a microwave radiating section of FIG. 1 inserted through the multi-lumen overmolded fluid hub of FIG. 3, in accordance with aspects of the present disclosure.

Referring to FIG. 4, the assembled view 400 of the microwave transmission and radiation component 100 and the multi-lumen overmolded fluid hub 300 is shown. The microwave transmission and radiation component 100 is inserted into the multi-lumen hub 300. Cannula 314 receives the coaxial feed line 106 and radiating section 106a of the microwave transmission and radiation component 100. The o-ring 115 (FIG. 2) is positioned in chamber 312 (FIG. 3) to secure the second section 113 of the transition head 110 adjacent the proximal end 301 of the multi-lumen hub 300 at a region 410.

The cannula 314 and the multi-lumen hub 300 define a longitudinal axis "X" therethrough. The microwave transmission cable assembly 102 defines a longitudinal axis "Y" extending therethrough. The longitudinal axis "X" is substantially perpendicular to the longitudinal axis "Y." Thus, the multi-lumen hub 300 is assembled at a 90-degree angle with respect to the microwave transmission cable assembly 102. As a result, the 90-degree interlocking geometry of the transition head 110 enables a 90-degree placement or positioning of the multi-lumen hub 300 with respect to the microwave transmission cable assembly 102.

Figure 5:
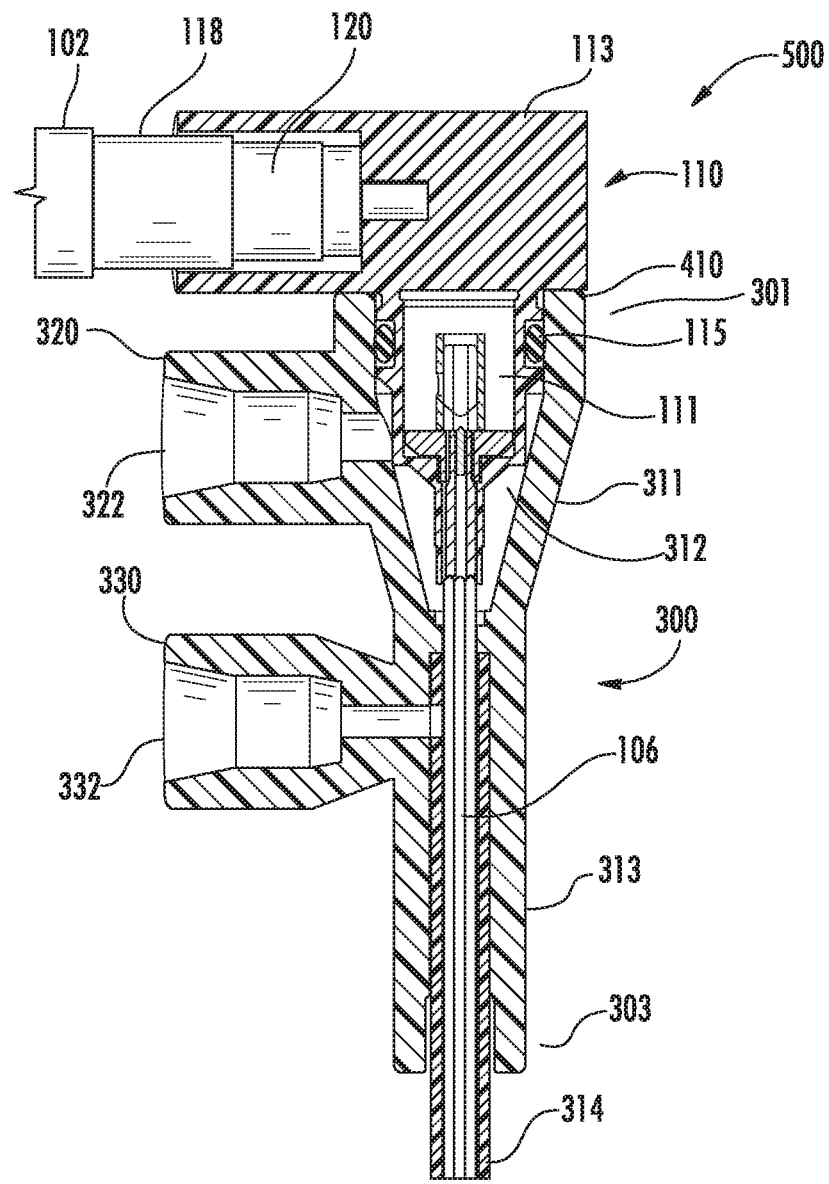
FIG. 5 is a cross-sectional view of the coaxial feedline having the microwave radiating section of FIG. 1 inserted into the multi-lumen overmolded fluid hub of FIG. 3, in accordance with aspects of the present disclosure.

Referring to FIG. 5, the first section 111 of the transition head 110 is inserted into or received within the chamber 312 of the body portion 310 of the multi-lumen hub 300. The second section 113 of the transition head 110 is secured adjacent the proximal end 301 of the multi-lumen hub 300 at a region 410. The second section 113 of the transition head 110 seals off the chamber 312 via the o-ring 115. The o-ring 115 sits at the proximal end 301 of the upper body portion 311 and within the chamber 312. The o-ring 115 circumferentially engages an inner surface of the chamber 312 to form a tight seal thereof.

Additionally, the cross-sectional view 500 illustrates a connecting member 120 for coupling the end 118 of the microwave transmission cable assembly 102 to the coaxial feed line 106. The connecting member 120 is fully positioned within the second section 113 of the transition head 110.

In FIG. 5, the inflow port 320 is substantially parallel to the outflow port 330. The inflow and outflow ports 320, 330 may be substantially in parallel to the microwave transmission cable assembly 102. Thus, the microwave transmission cable assembly 102, the inflow port 320, and the outflow port 330 are all substantially perpendicular to the multi-lumen hub 300 and with the coaxial feed line 106. The coaxial feed line 106 extends the length of the cannula 314. The cannula 314 is in fluid communication with both the inflow port 320 and the outflow port 330 such that a coolant flows along the coaxial feed line 106 and around the radiating section 106a formed on a distal portion of the coaxial feed line 106.

Figure 6:
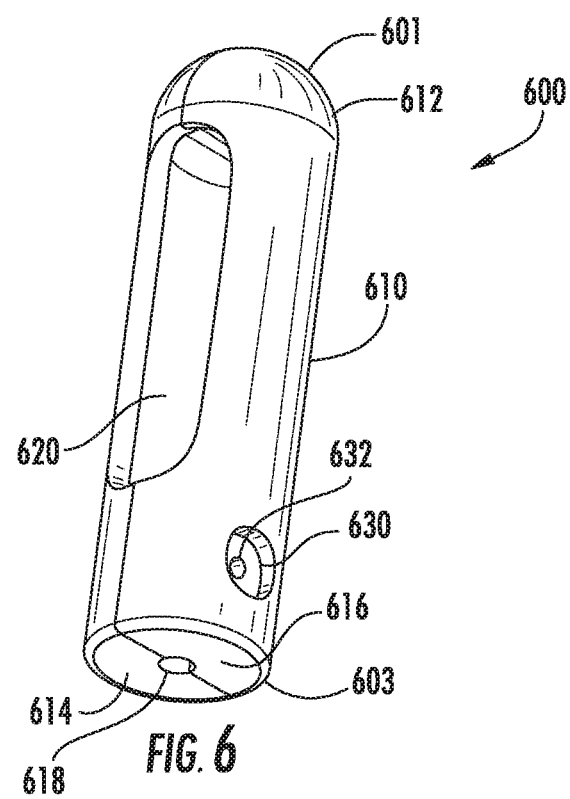
FIG. 6 is a perspective view of a sliding spindle, in accordance with aspects of the present disclosure.
Figure 7:
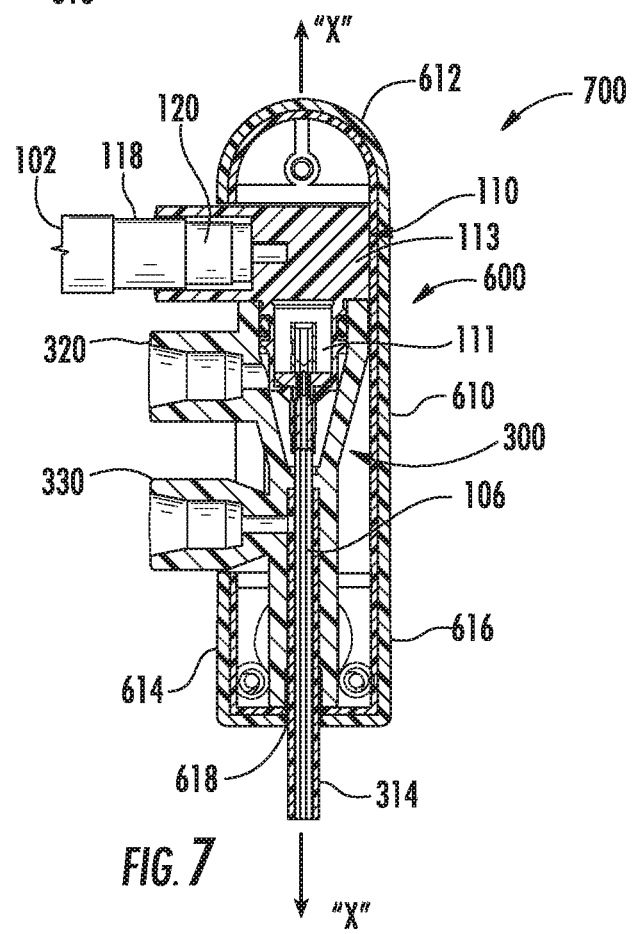
FIG. 7 is a cross-sectional view of the sliding spindle of FIG. 6 assembled onto at least the multi-lumen overmolded fluid hub of FIG. 3, in accordance with aspects of the present disclosure.

Referring to FIG. 6, an actuator is shown, such as for example, a sliding spindle 600 that includes a body portion 610 having a proximal portion 601 and a distal portion 603. The proximal portion 601 defines, for example, a dome-shaped portion 612. The body portion 610 further defines an opening 620, as well as a pair of recesses 630. The recesses 630 are positioned on opposed sides of the distal portion 603 of the body portion 610. The recesses 630 are offset from the opening 620. The offset may be a 90-degree offset. Each of the pair of recesses 630 includes an aperture 632. The body portion 610 is defined by a first body section 614 and a second body section 616 which are joined to form the body portion 610. The distal portion 603 of the sliding spindle 600 further defines an aperture 618. The aperture 618 is configured to allow the coaxial cannula 314 to pass therethrough, as discussed below with reference to FIG. 7.

The elongated body portion 610 of the sliding spindle 600 is assembled over the multi-lumen hub 300 and the transition head 110. The second section 113 of the transition head 110, the inflow port 320, and the outflow port 330 extend through the opening 620 (FIG. 6) of the body portion 610. Both the first section 111 and the second section 113 of the transition head 110 are at least partially enclosed within the sliding spindle 600. The dome-shaped portion 612 of the body portion 610 of the spindle 600 is secured adjacent the second section 113 of the transition head 110. The cannula 314 of the multi-lumen hub 300 extends through the aperture 618 of the sliding spindle 600. The cannula 314 defines a longitudinal axis "X" extending through the multi-lumen hub 300 and the sliding spindle 600.

Figure 8:
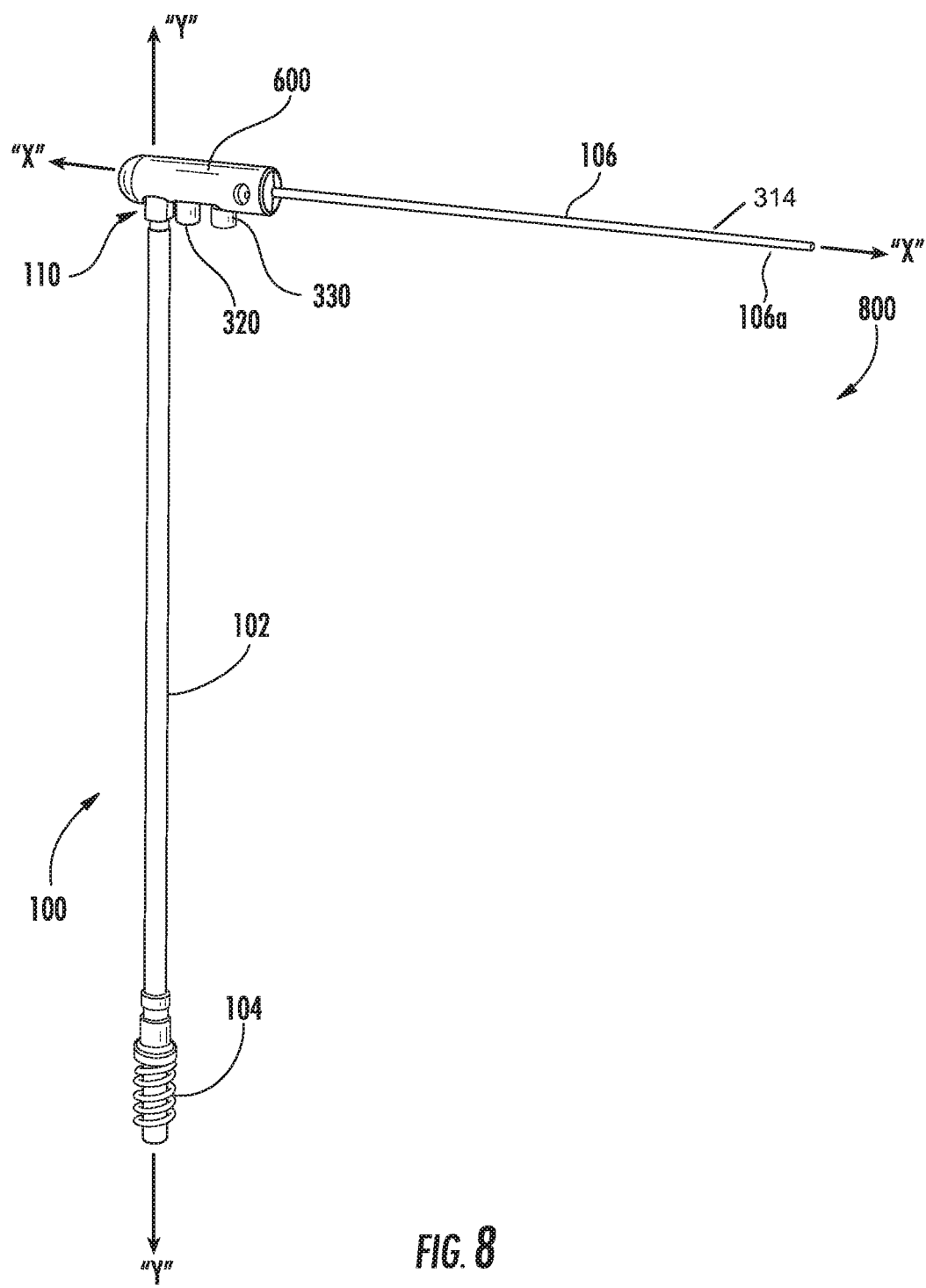
FIG. 8 is a perspective view of the sliding spindle of FIG. 6 assembled onto the microwave transmission and radiation component of FIG. 1, in accordance with aspects of the present disclosure.

Referring to FIG. 8, the assembled view 800 of the microwave transmission and radiation component 100 and the multi-lumen overmolded fluid hub 300 and the sliding spindle 600 is shown. The microwave transmission and radiation component 100 is inserted into the multi-lumen hub 300 such that the coaxial feed line 106 and radiating section 106a are received within the cannula 314. Then the sliding spindle 600 is assembled over the multi-lumen hub 300. The cannula 314 and the multi-lumen hub 300, and the sliding spindle 600 define a longitudinal axis "X" therethrough. The microwave transmission cable assembly 102 defines a longitudinal axis "Y" extending therethrough. The longitudinal axis "X" is substantially perpendicular to the longitudinal axis "Y." Thus, the sliding spindle 600 and the multi-lumen hub 300 are assembled at a 90-degree angle with respect to the microwave transmission cable assembly 102.

In FIG. 9, the recess 630 is a circular recess defined at the distal portion 603 of the body portion 610 of the sliding spindle 600. In the embodiment depicted in FIG. 9, a similar recess 630 on the other side of the sliding spindle 600 is present (not shown). Therefore, a pair of recesses 630 are defined on diametrically opposed surfaces of the distal portion 603 of the body portion 610. The recesses 630 are each configured to receive a pair of pins 1010, 1020 shown in FIG. 10. The first pin 1010 includes a first section 1011 and a second section 1013. The second pin 1020 is similar to the first pin 1010, but is shown in an inverted configuration with respect to the first pin 1010. The second pin 1020 includes a first section 1021 and a second section 1023. The second pin 1020 also includes a rod 1025 extending away from the first section 1021. The first section 1021 defines an annular recess 1027 surrounding the rod 1025. The rod 1025 is configured to be received within an aperture 632 of the recess 630 to secure the second pin 1020 to the recess 630 of the sliding spindle 600. As can be appreciated, a spring (not shown) may be received in the annular recess 1027 to push the pins 1010 and 1020 away from the body portion 610 of the sliding spindle 600, when the pins 1010, 1020 are received within the recesses 630, as shown in FIG. 11, and in accordance with embodiments described below.

Figure 12:
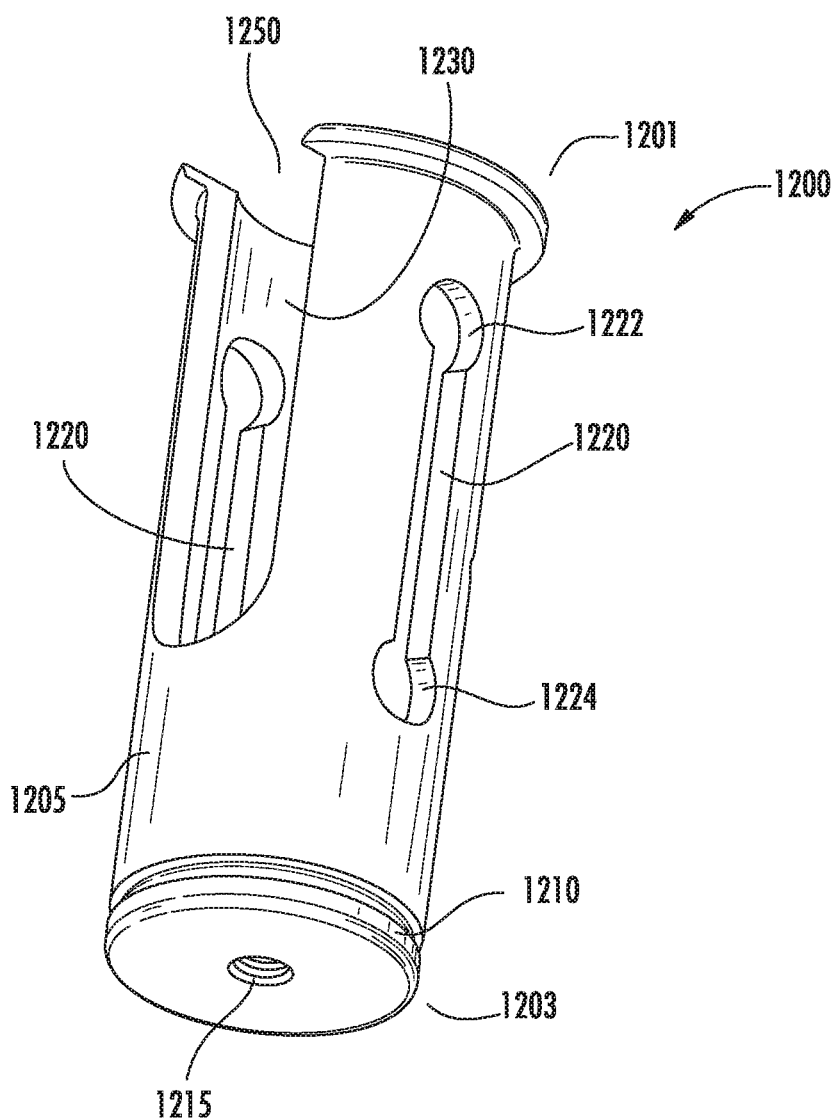
FIG. 12 is a perspective view of a locking spindle, in accordance with aspects of the present disclosure.
Figure 13:
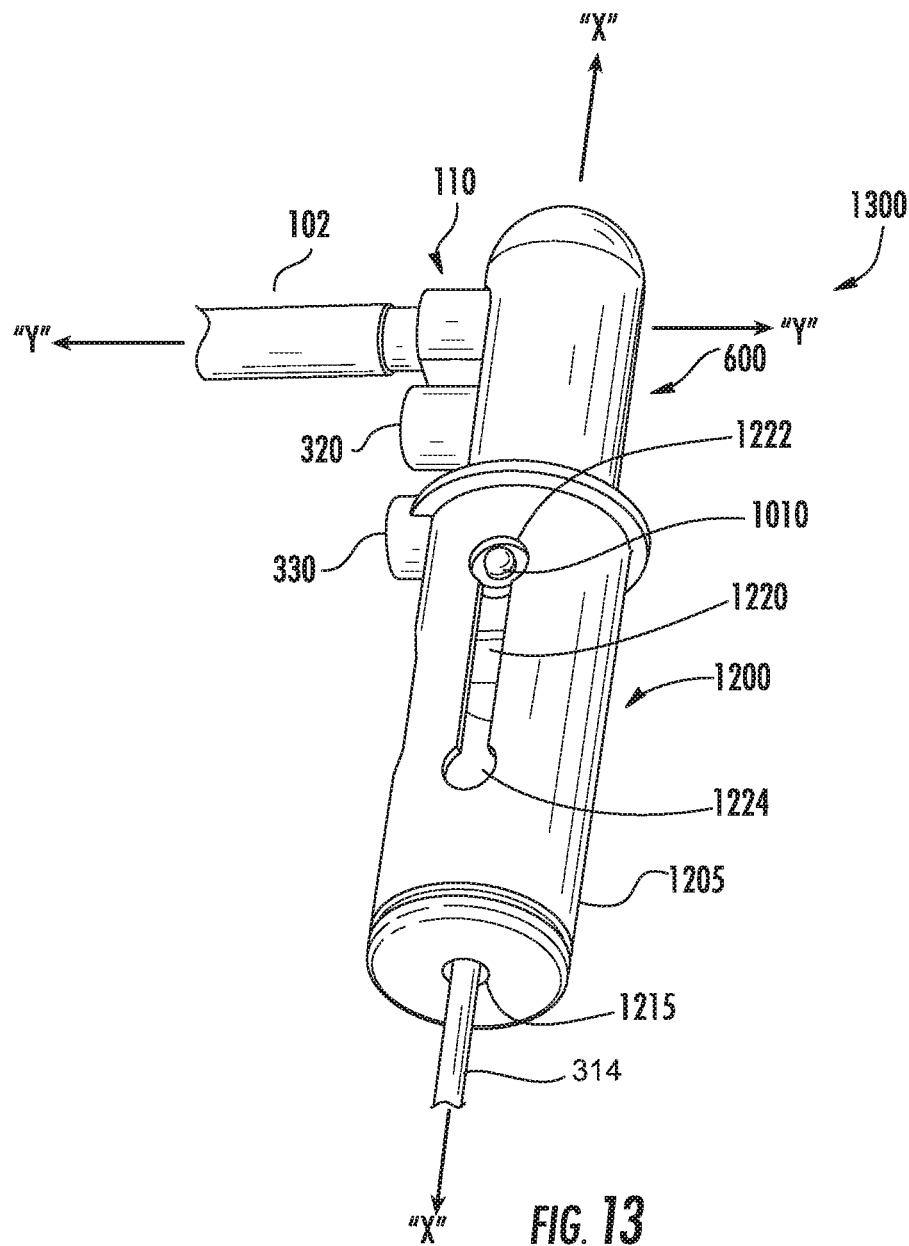
FIG. 13 is an enlarged view of the locking spindle of FIG. 12 assembled onto the sliding spindle of FIG. 6, in accordance with aspects of the present disclosure.

Referring to FIG. 12, the locking spindle 1200 includes a body portion 1205 having a proximal end 1201 and a distal end 1203. The distal end 1203 includes a retaining ring 1210. The body portion 1205 includes an opening 1250 for receiving the inflow port 320, the outflow port 330, and the microwave transmission cable assembly 102 (FIG. 13). The body portion 1205 further includes a pair of longitudinal slots 1220. As shown in FIG. 12, the longitudinal slots 1220 separate a first circular end 1222 from a second circular end 1224. The pair of longitudinal slots 1220 and their respective first and second circular ends 1222, 1224 are configured to receive the pins 1010, 1020 (FIG. 10) as will be described in further detail below. The distal end 1203 may further define an aperture 1215 for receiving the cannula 314 (FIG. 13) into which the feed line 106 and radiating section 106a have been inserted. The longitudinal slots 1220 may also be referred to as camming surfaces. The first and second circular ends 1222, 1224 may be of equal size.

The body portion 1205 also includes an opening or cut-out 1230. The opening 1230 extends a length of the body portion 1205 such that the inflow port 320, the outflow port 330, and the distal end 103 of the microwave transmission cable assembly 102 are accommodated therein (FIG. 16B). The opening 1230 may be offset from the pair of longitudinal slots 1220. The offset may be a 90-degree offset.

Referring to FIG. 13, the assembled view 1300 illustrates the sliding spindle 600 assembled over the multi-lumen hub 300 received in the locking spindle 1200 such that the pins 1010, 1020 of the sliding spindle 600 engage their respective longitudinal slots 1220 of the locking spindle 1200. The pins 1010, 1020 slide along their respective longitudinal slots 1220 such that the pins 1010, 1020 travel from or between the first circular end 1222 and the second circular end 1224. A biasing means, such as a spring (not shown) forces the pins 1010, 1020, away from the body portion 610 of the sliding spindle 600 and into engagement with the circular end 1222, as shown in FIG. 13.

Figure 14A:
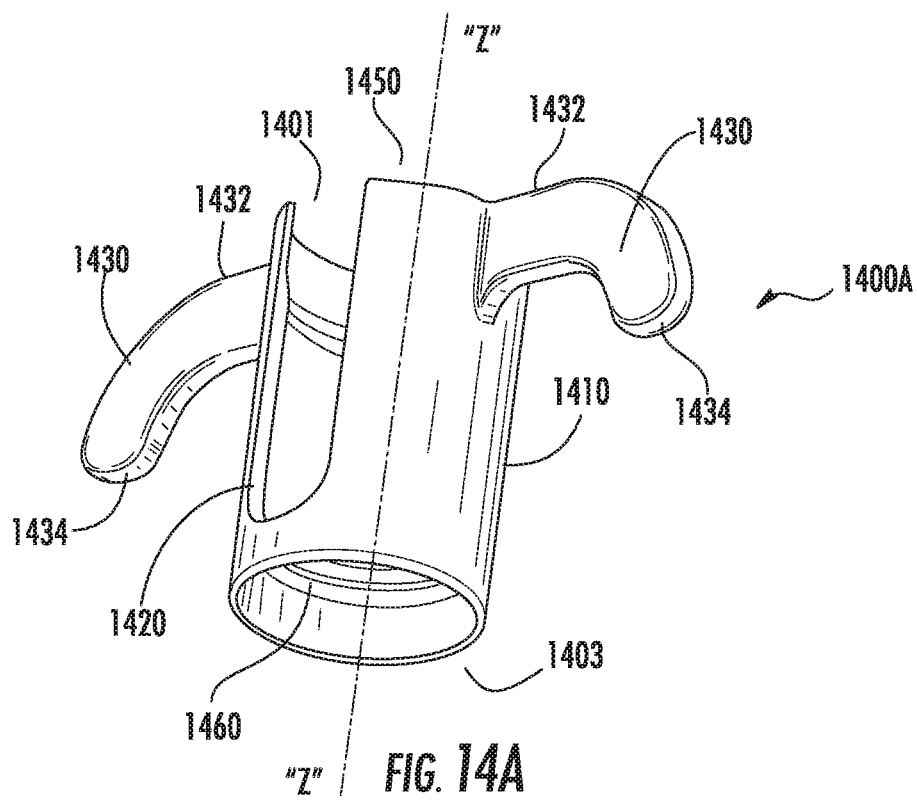
FIG. 14A is a perspective view of a first embodiment of a control ring, in accordance with aspects of the present disclosure.

Referring to FIG. 14A, an actuator, such as a control ring 1400A is shown and includes a body portion 1410 having a proximal end 1401 and a distal end 1403. The proximal end 1401 has a pair of projections 1430 extending outward from the body portion 1410. The pair of projections 1430 defines a first arm section 1432 and a second arm section 1434. The first arm section 1432 is substantially perpendicular to the body portion 1410 or the longitudinal axis "Z" defined through the body portion 1410. The second arm portion 1434 is, for example, a curved portion. The pair of projections 1430 forms a handle member for manual manipulation. The body portion 1410 also defines an opening or cut-out 1420 for receiving or accommodating therein the inflow port 320, the outflow port 330, and the microwave transmission cable assembly 102 (FIG. 17). The control ring 1400A further defines a channel or through passage 1450 therethrough. The interior surface of the control ring 1400A may include one or more stops 1460.

Figure 14B:
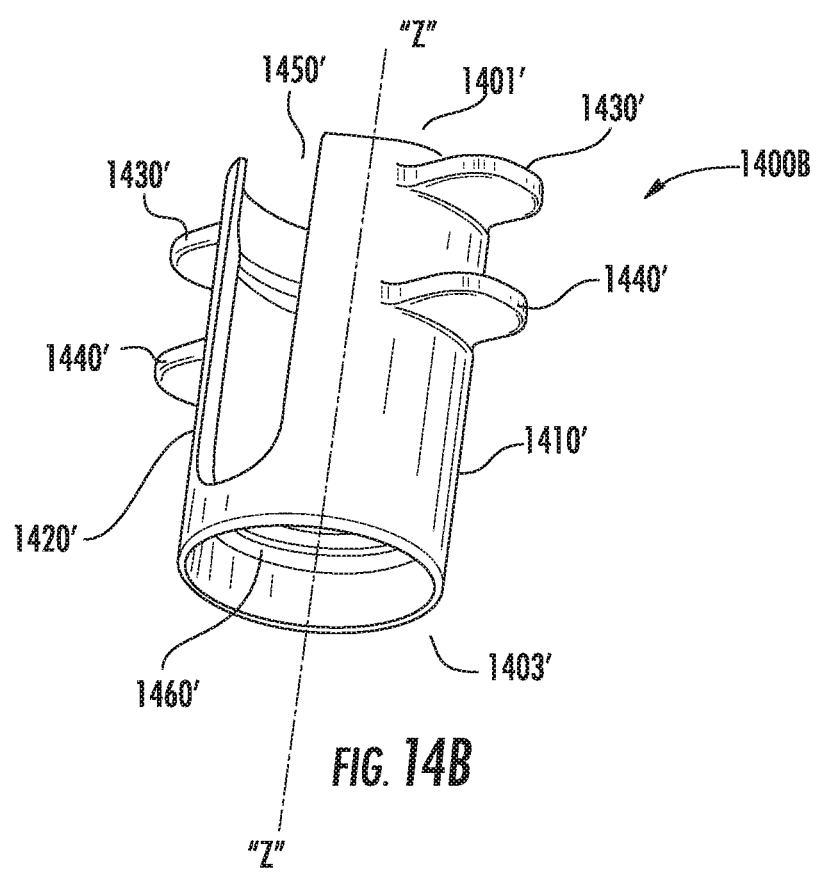
FIG. 14B is a perspective view of a second embodiment of a control ring, in accordance with aspects of the present disclosure.

Referring to FIG. 14B, the control ring 1400B includes a body portion 1410' having a proximal end 1401' and a distal end 1403'. The proximal end 1401' has a first pair of projections 1430' extending outward from the body portion 1410' and a second pair of projections 1440' extending outward from the body portion 1410'. The first and second pair of projections 1430', 1440' may be substantially perpendicular to the body portion 1410' or the longitudinal axis "Z" defined through the body portion 1410'. The first and second pair of projections 1430', 1440' may form a handle member for manual manipulation. The body portion 1410' also defines an opening or cut-out 1420' for receiving or accommodating therein the inflow port 320, the outflow port 330, and the microwave transmission cable assembly 102 (FIG. 17). The control ring 1400B further defines a channel 1450' therethrough. The interior surface of the control ring 1400B may include one or more stops 1460'.

Both the sliding spindle 600 and the control arm 1400A are described herein as an actuator. One of skill in the art will recognize that in accordance with the present disclosure these two actuators may operate individually or in concert, and they may act on different components of the assemblies described herein.

Figure 15A:
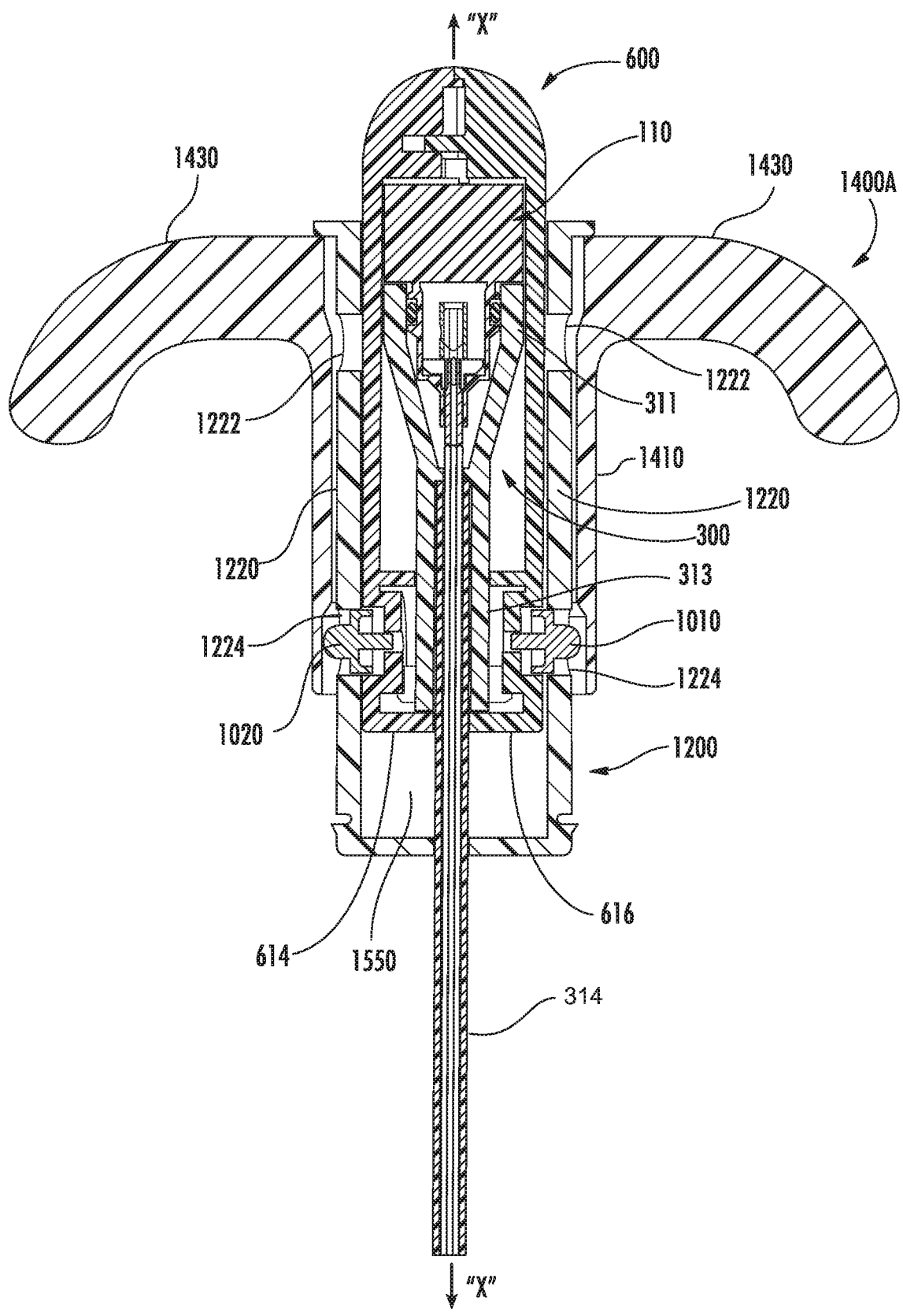
FIG. 15A is a cross-sectional view of the control ring of FIG. 14A assembled onto the locking spindle of FIG. 12, where the control ring is in a first or deployed position, in accordance with aspects of the present disclosure.

The deployment of the cannula 314 housing the coaxial feed line 106 and radiating section 106a will now be described with reference to FIGS. 15A and 15B. FIG. 15A is a cross-sectional view 1500A of the control ring 1400A of FIG. 14A assembled onto the locking spindle 1200 of FIG. 12 and sliding spindle 600 of FIG. 11, where the cannula 314 is in a deployed position, in accordance with aspects of the present disclosure.

FIG. 15A, the control ring 1400A is assembled onto or mounted on the locking spindle 1200 such that the pins 1010, 1020 of the sliding spindle 600 travel along the slotted openings 1220 of locking spindle 1200. The opening 1420 (FIG. 14A) may extend a substantial length of the body portion 1410 of the control ring 1400A. In the deployed position, the sliding spindle 600 rests in the lower portion of the area 1550 defined by the locking spindle 1200, and the pins 1010, 1020 rest within the second circular ends 1224 proximate the distal end 1403 of the control ring 1400A. The second sections 1013, 1023 (FIG. 10) of the pins 1010, 1020, respectively, are protruding members such that when the pins are depressed into the recesses 630 of the sliding spindle 600, they permit the movement of the sliding spindle 600 relative to the locking spindle 1200 via slotted opening 1220 and prevent the removal of the sliding spindle 600 from the locking spindle 1200.

Figure 15B:
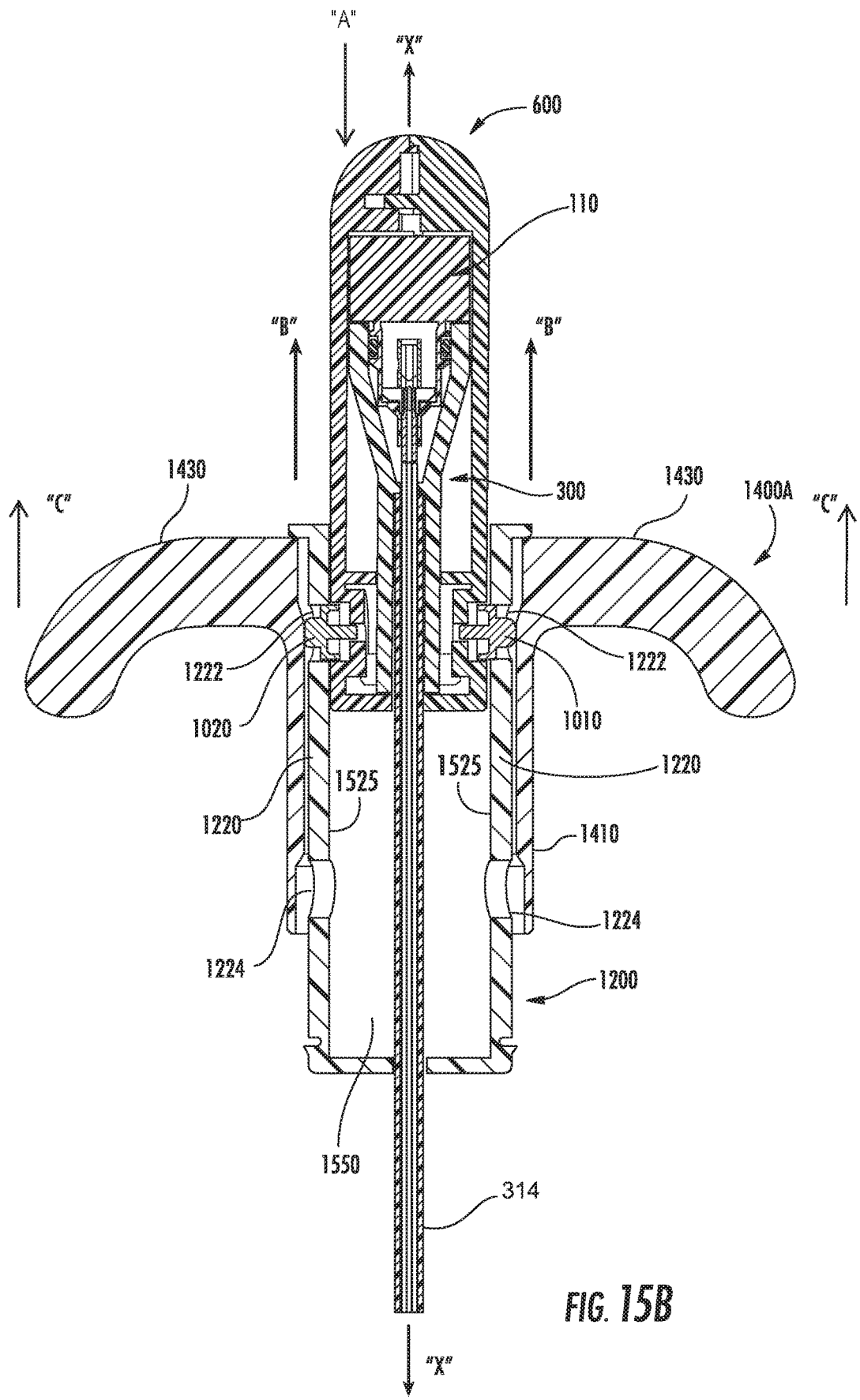
FIG. 15B is a cross-sectional view of the control ring of FIG. 14A assembled onto the locking spindle of FIG. 12, where the control ring is in a second or retracted position, in accordance with aspects of the present disclosure.

FIG. 15B is a cross-sectional view 1500B of the control ring 1400A of FIG. 14A assembled onto the locking spindle 1200 of FIG. 12 and sliding spindle 600 of FIG. 11, where the cannula 314 is in a retracted position, in accordance with aspects of the present disclosure.

In the retracted position, the sliding spindle 600 rests in the upper portion of the area 1550 defined by the locking spindle 1200. In both these configurations, the transition head 110 remains secured to the multi-lumen hub 300 within the sliding spindle 600, and the cannula 314 moves relative to the locking spindle 1200. In the retracted position, the pins 1010, 1020 rest within the first circular ends 1222 or at the proximal end 1401 of the control ring 1400A.

Additionally, since the control ring 1400A is mounted onto the locking spindle 1200, the control ring 1400A also moves relative to the sliding spindle 600. Thus, when a holding force "A" is applied to the sliding spindle, and an actuating force "C" is applied to the pair of projections 1430, of the control ring 1400A such that the sliding spindle 600 does not move, the control ring 1400A moves in a direction "B." This movement results in the change depicted by comparison of FIG. 15B, retracted position, to FIG. 15A, deployed position. In such a transition, the pins 1010, 1020 travel along their respective longitudinal slots 1220 between the first circular ends 1222 and the second circular ends 1224. The sliding spindle 600 engages the inner surface 1525 of the locking spindle 1200 within the area 1550. Thus, the locking spindle 1200 selectively locks the sliding spindle 600 between an extended position and a retracted position. As a result, the cannula 314 may be extended and retracted based on relative movement of the sliding spindle 600 and the control ring 1400A and the locking spindle 1200.

Figure 16A:
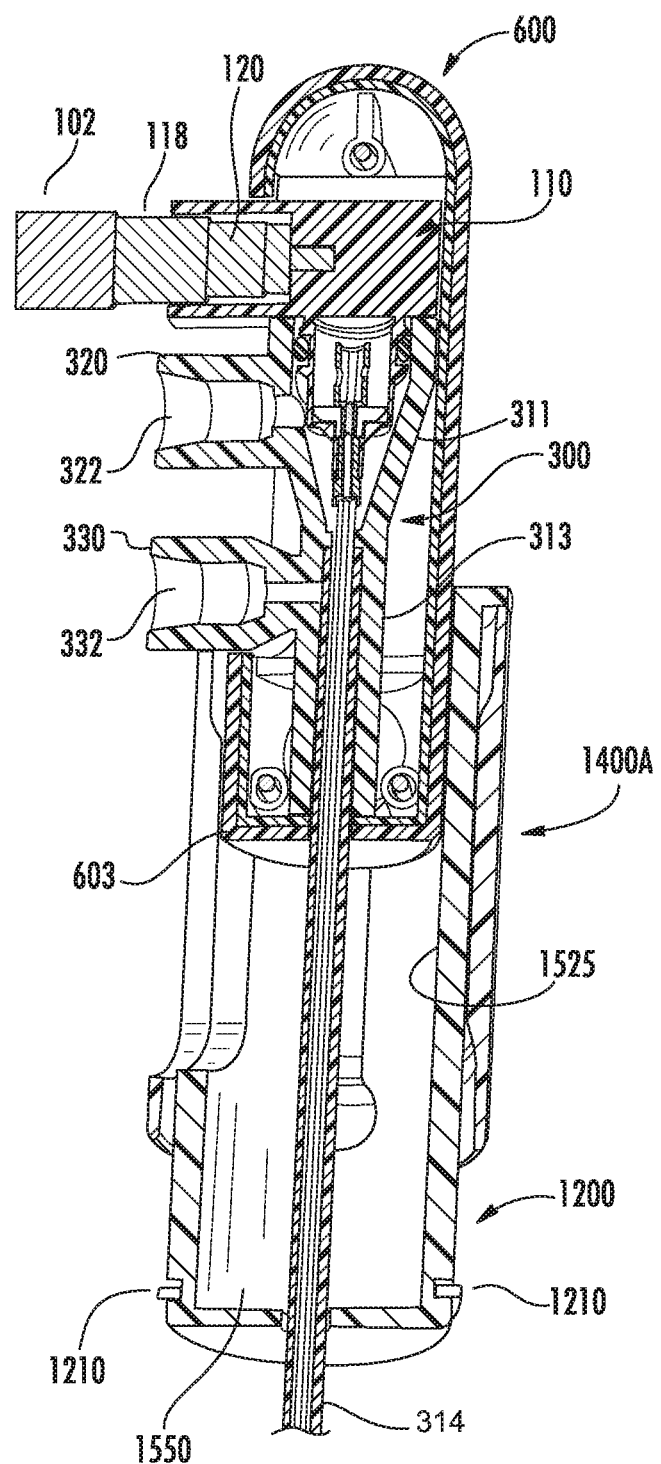
FIG. 16A is a cross-sectional view of the control ring of FIG. 14A assembled onto the locking spindle of FIG. 12, where the control ring is in the second position, in accordance with aspects of the present disclosure.
Figure 16B:
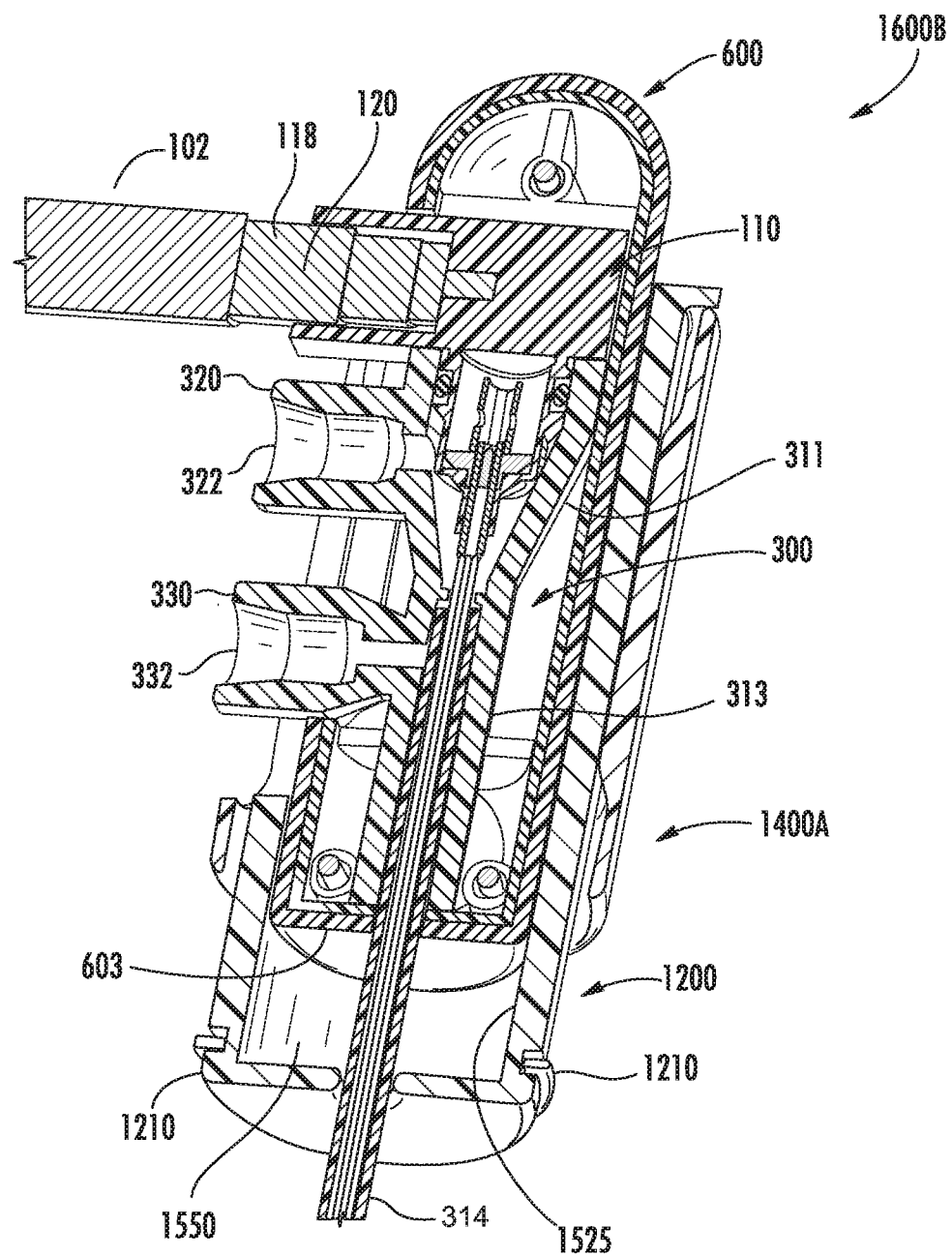
FIG. 16B is a cross-sectional view of the control ring of FIG. 14A assembled onto the locking spindle of FIG. 12, where the control ring is in the first position, in accordance with aspects of the present disclosure.

FIG. 16A shows an alternate view of the control ring 1400A of FIG. 14A assembled onto the locking spindle 1200 of FIG. 12, where the cannula 314 and sliding spindle 600 are in the retracted position. Similarly, FIG. 16B shows an alternate view of the control ring 1400A of FIG. 14A assembled onto the locking spindle 1200 of FIG. 12, where cannula 314 is placed in the deployed position. FIGS. 16A and 16B show the inflow port 320, the outflow port 330, and the microwave transmission cable assembly 102 extending through the opening 1230 (FIG. 12) of the locking spindle 1200 and the opening 1420 (FIG. 14A) of the control ring 1400A. In addition, the inflow port 320, the outflow port 330, and the distal end 103 of the microwave transmission cable assembly 102 move within the area defined by the opening 1230 of the locking spindle 1200 and the opening 1420 of the control ring 1400A (when transitioning between extended and retracted positions).

As noted above with reference to FIGS. 16A and 16B, the inflow port 320, the outflow port 330, and the distal end 103 of the microwave transmission cable assembly 102 move within the area defined by the opening 1230 (FIG. 12) of the locking spindle 1200 and the opening 1420 of the control ring 1400A (when transitioning between extended and retracted positions). The openings 1230 and 1420 overlap each other. FIG. 17 also provides an alternate perspective view of the sliding spindle 600, within the locking spindle 1200, and the control ring 1400A.

FIG. 18 depicts a nose cone 1800 for connection to locking spindle 1200. The nose cone 1800 includes a body portion 1810 defining an upper body section 1811 and a lower body section 1813. The upper body section 1811 includes a cut-out section 1815. The body portion 1810 has a distal portion 1820 formed at the lower body section 1813. The distal portion 1820 has an aperture 1830.

Figure 19:
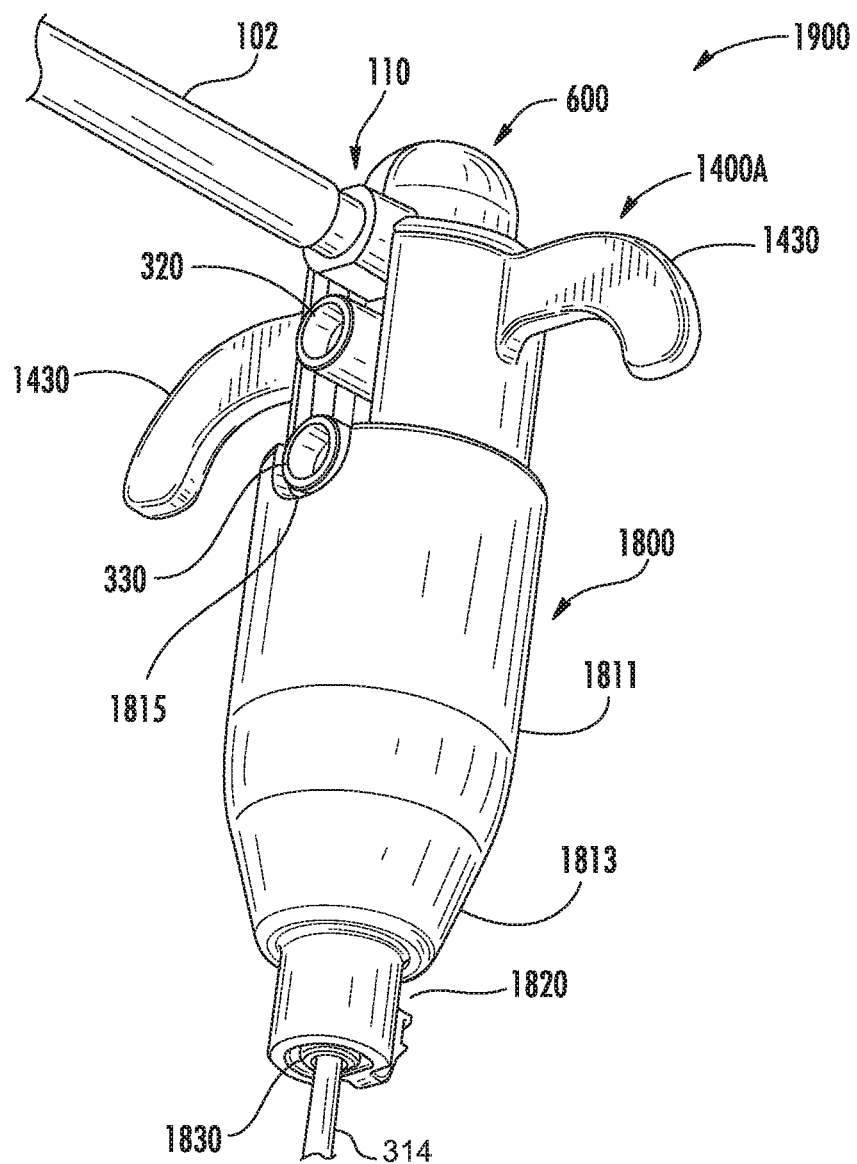
FIG. 19 is a perspective view of the nose cone of FIG. 18 assembled onto the control ring of FIG. 14A, in accordance with aspects of the present disclosure.

Referring to FIG. 19, the upper body portion 1811 is configured to receive the distal end 1203 of the locking spindle 1200 (FIG. 12) and the distal end 1403 (FIG. 17) of the control ring 1400A. The cut-out section 1815 of the upper body portion 1811 is configured to surround the outflow port 330. The cannula 314 extends through the aperture 1830 of the distal portion 1820 of the nose cone 1800. Thus, the aperture 1830 is adapted and dimensioned to receive the cannula 314.

Figure 20:
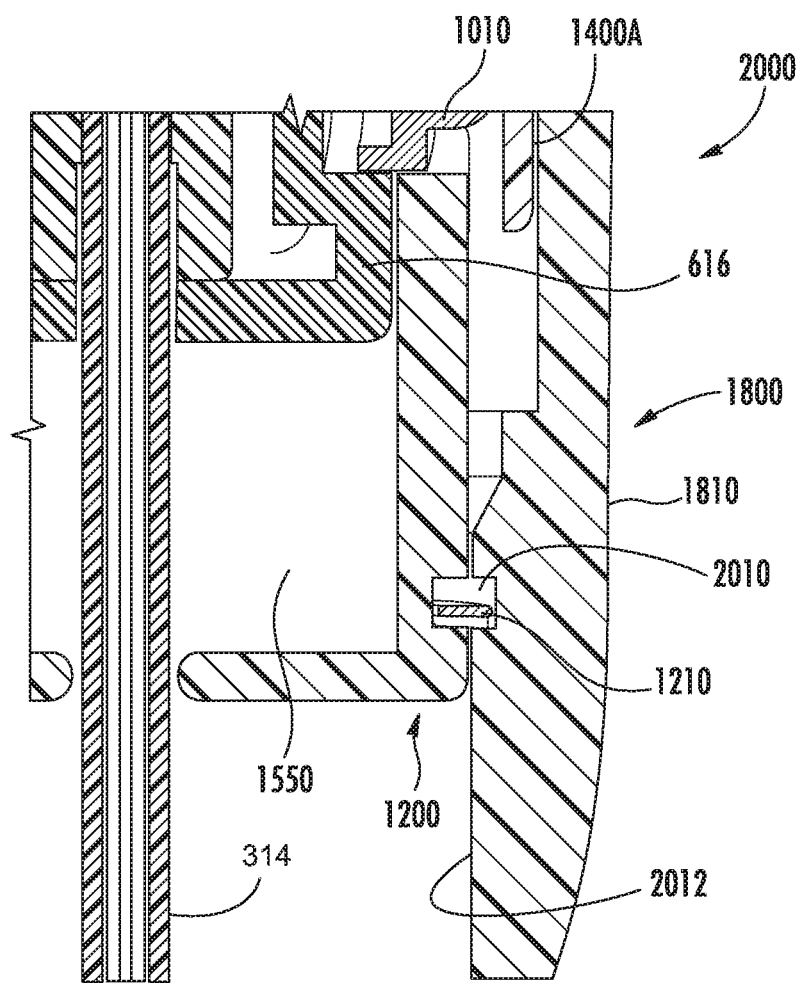
FIG. 20 is a cross-sectional view of a portion of the nose cone, the nose cone connected to a retaining ring of the locking spindle to secure the nose cone to the locking spindle, in accordance with aspects of the present disclosure.

As shown in FIG. 20, the nose cone 1800 includes a recess 2010 on an inner surface 2012 thereof for receiving a retaining ring 1210 of the locking spindle 1200. The recess 2010 is an annular recess defined along the inner surface 2012 of the nose cone 1800. The retaining ring 1210 interacts with the recess 2010 to secure the nose cone 1800 to the locking spindle 1200.

Figure 21:
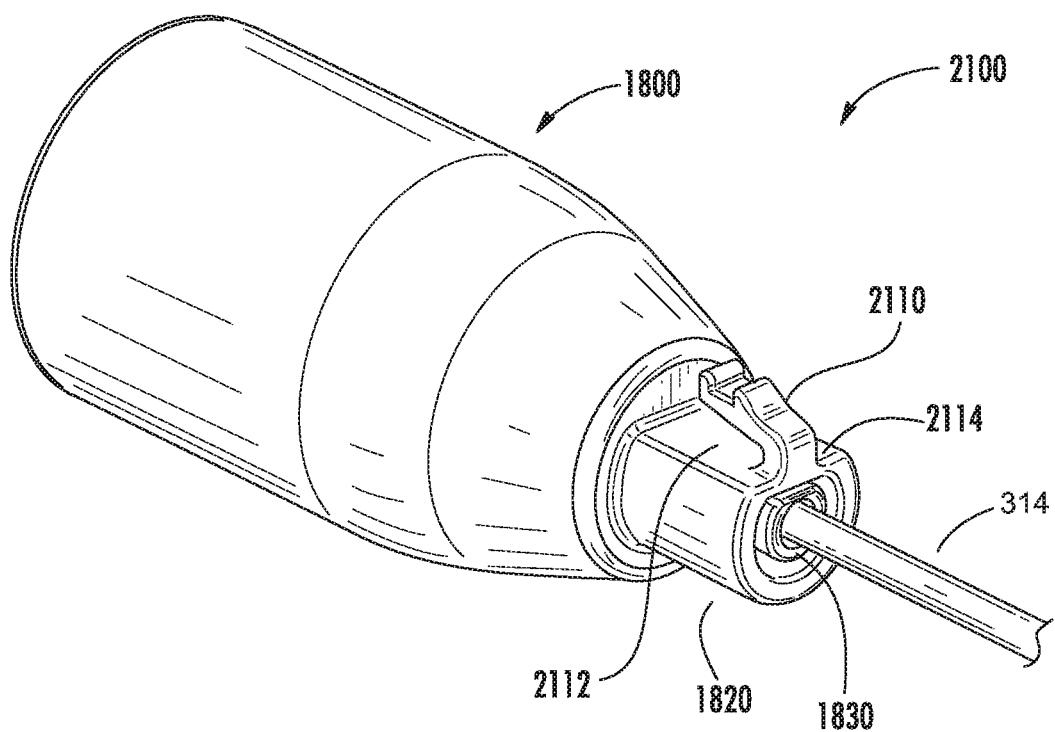
FIG. 21 is an enlarged view of the nose cone of FIG. 18 illustrating a hinge component, in accordance with aspects of the present disclosure.

In FIG. 21, the locking mechanism 2110 is shown positioned on a distal end 2114 of a flat surface 2112 of the distal portion 1820 of the nose cone 1800. The locking mechanism 2110 is configured to mate with a trocar/cannula assembly described below with reference to FIGS. 23A-23D.

Figure 22:
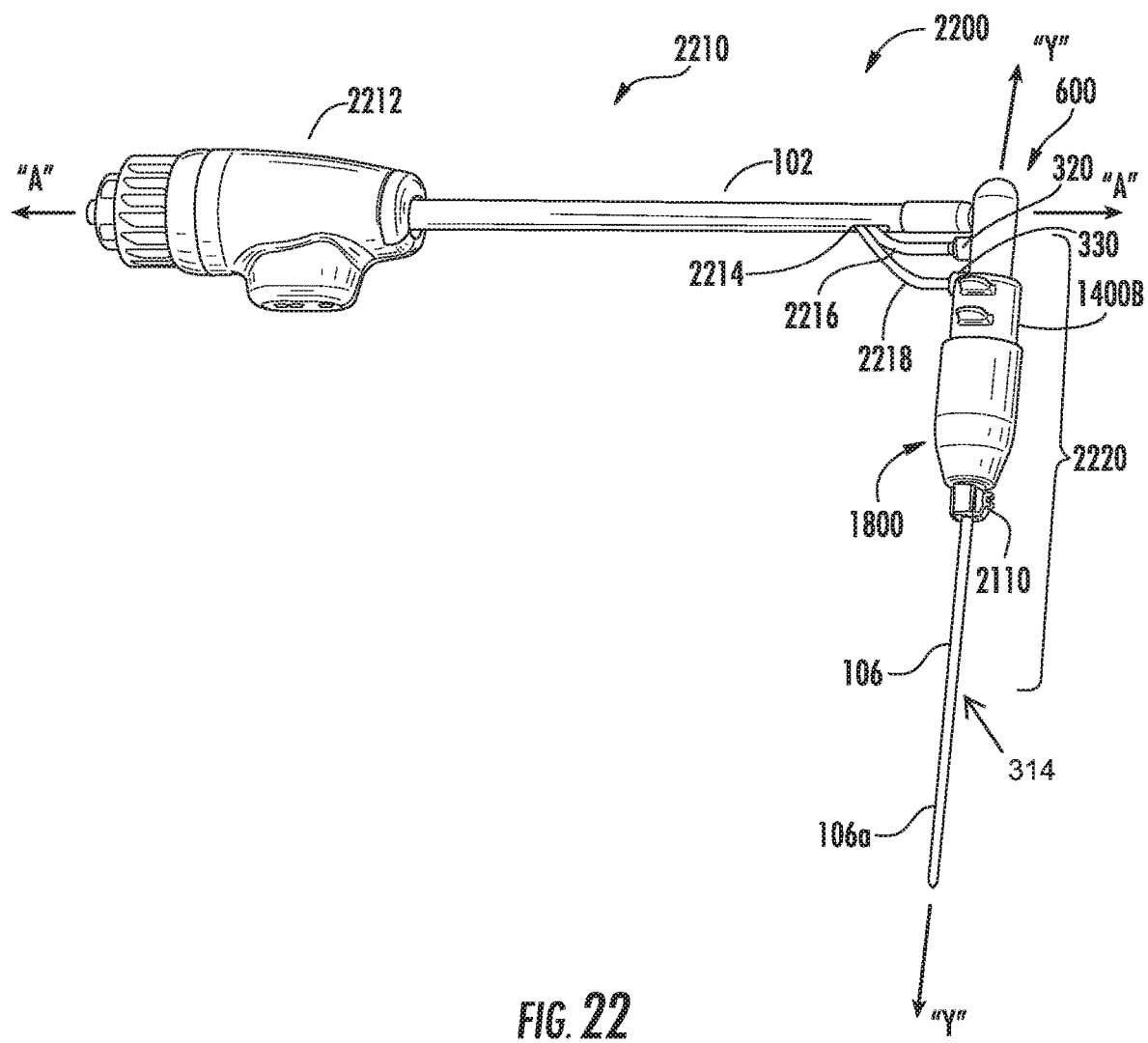
FIG. 22 is a perspective view of a surgical system including a microwave catheter and an access channel device assembled in a manner described with reference to FIGS. 1-20, in accordance with aspects of the present disclosure.

FIG. 22 depicts a fully assembled microwave ablation assembly 2200 including a housing 2212 covering spring-biased coupling element 104 for connection to a microwave generator. The microwave transmission cable assembly 102 may include covering having a slot 2214 through which a first fluid flow channel 2216 and a second fluid flow channel 2218 exit. The first fluid flow channel 2216 is connected to the inflow port 320 and the second fluid flow channel is connected to the outflow port 330. Though not shown, the microwave generator may include a fluid source and enable connection of the fluid source through the housing 2212.

Insertion and deployment of the microwave ablation assembly 2200 is described with reference to FIGS. 23A-24.

Figure 23A:
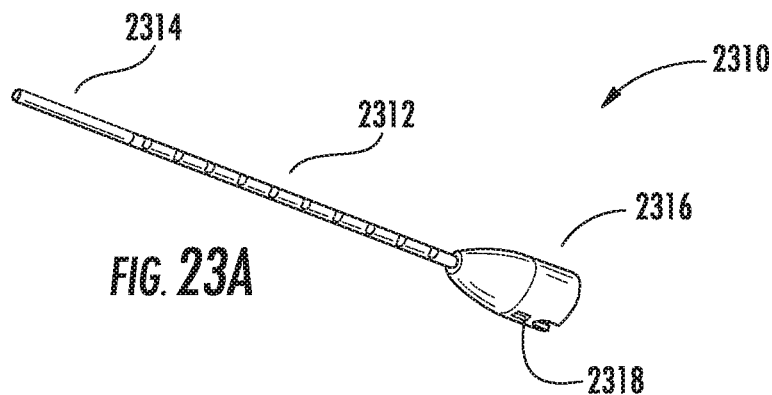
FIG. 23A is a perspective view of a cannula, in accordance with aspects of the present disclosure.
Figure 23B:
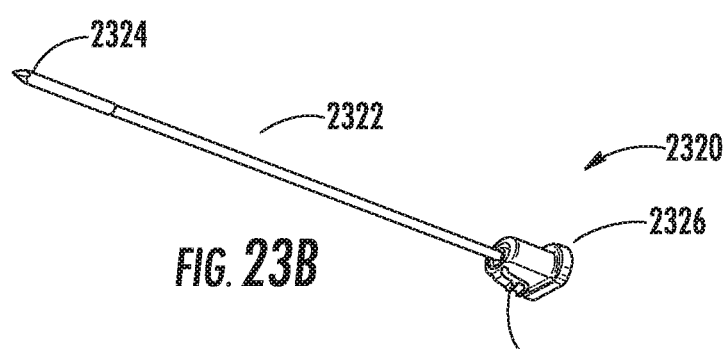
FIG. 23B is a perspective view of a trocar, in accordance with aspects of the present disclosure.
Figure 23C:
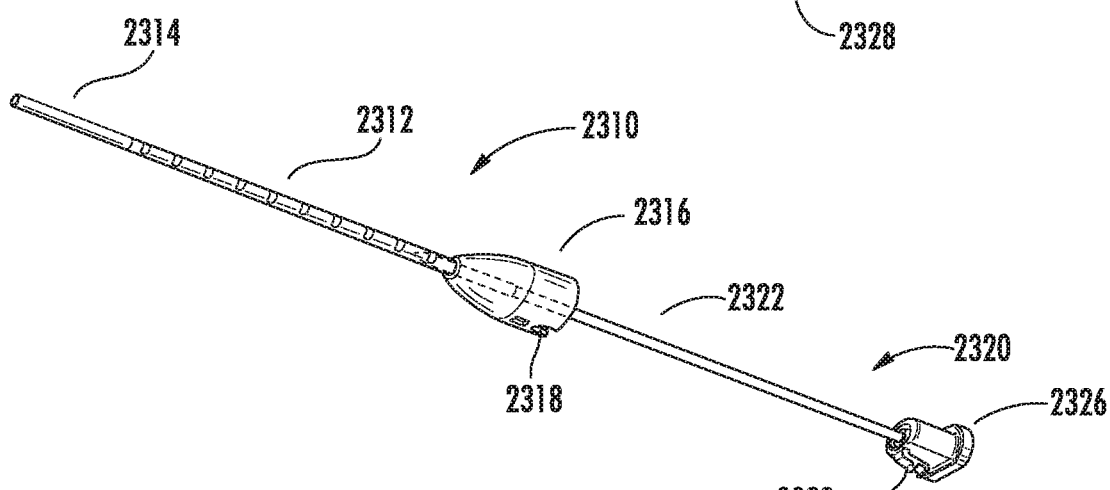
FIG. 23C is a perspective view of the trocar of FIG. 23B being inserted within the cannula of FIG. 23A, in accordance with aspects of the present disclosure.
Figure 23D:
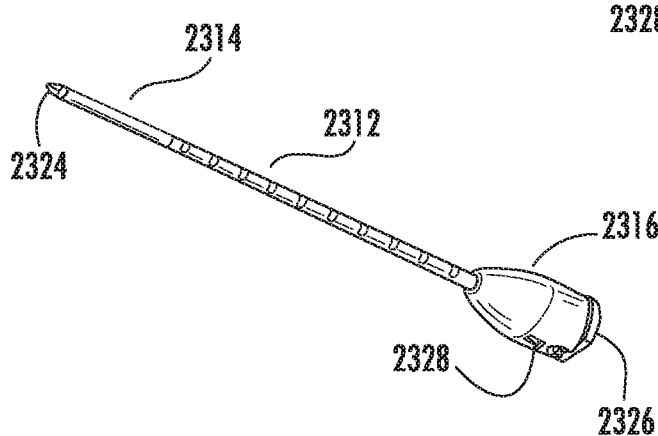
FIG. 23D is a perspective view of the trocar of FIG. 23B fully inserted within the cannula of FIG. 23A, in accordance with aspects of the present disclosure.

FIG. 23A depicts a rigid cannula 2310 including a housing 2316 connected to a shaft 2312 having a distal portion 2314. The housing 2316 includes a slot 2318 for receiving a locking mechanism 2328 or 2110. FIG. 23B shows the trocar 2320, which includes a retaining member 2326 connected to a shaft portion 2322 having a distal tip 2324. The retaining member 2326 includes a locking mechanism 2328. Referring now to FIGS. 23C and 23D, the locking mechanism 2328 of the trocar 2320 mates with the slot 2318 of the housing 2316 of the cannula 2310. The locking mechanism 2328 secures the trocar 2320 to the cannula 2310. The trocar 2320 is thus releasably coupled to the cannula 2310. The distal tip 2324 may be a relatively pointed tip to pierce through tissue.

Typically a clinician, when performing for example a liver ablation procedure, will acquire a series of images to identify the location of a tumor or lesion for ablation. Once identified, the clinician will seek to place the cannula 2310 and trocar 2320 assembly as shown in FIG. 23D proximate that tumor or lesion. This placement may be performed through a variety of techniques including under fluoroscopy, ultrasound, MRI, and CT imaging techniques either alone or in combination with one or more navigation techniques, such as electromagnetic navigation. Once the cannula 2310 and trocar 2320 assembly is positioned in a desired location within a patient proximate the tumor or lesion, the trocar 2320 may be removed. The cannula 2310 remains in place ready to receive the microwave ablation assembly 2200 or where appropriate the performance of one or more pre-treatment biopsies.

The microwave ablation assembly 2200 may then be placed within the cannula 2310 at the desired location proximate the tumor or lesion and secured to the cannula 2310 via locking mechanism 2110 on the nose cone 1800 and slot 2310 on the housing 2316 of the cannula 2310. However, to protect the feed line 106 and radiating section 106a, within the cannula 314, the cannula 314 is not yet deployed from the cannula 2310. To deploy the cannula 314, within which is housed the feed line 106 and, more specifically, the radiating section 106a, the control ring 1400A and locking spindle 1200 must be compressed relative to the sliding spindle 600. By the relative movement of the locking spindle over the sliding spindle 600 (which is preferably held stationary), the cannula 2310 is retracted relative to the cannula 314, exposing the cannula 314, and specifically, the radiating section 106a housed therein.

Figure 24:
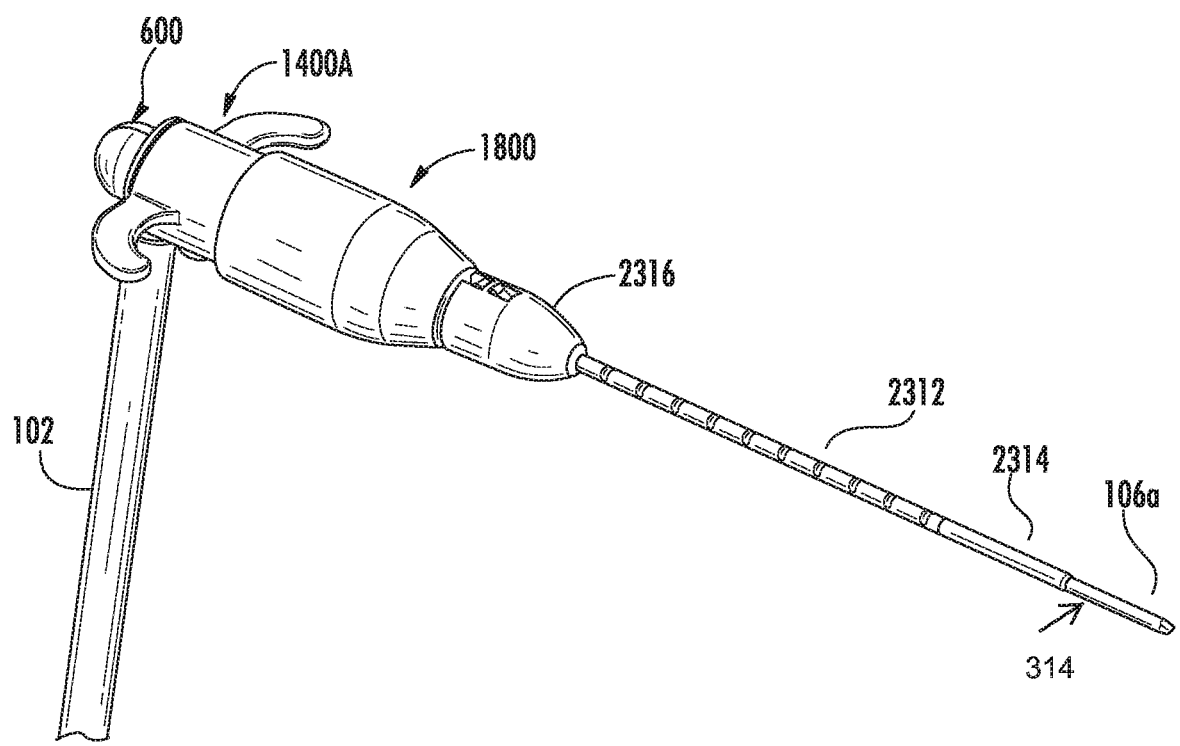
FIG. 24 is a perspective view of the cannula/trocar assembly of FIG. 23D mounted onto the nose cone of FIG. 18 and the microwave radiation section of FIG. 1, in accordance with aspects of the present disclosure.

FIG. 24 shows the cannula 314 extended beyond the distal end of the cannula 2310. In this position, the cannula 2310 has been retracted, thus exposing cannula 314 and the radiating section 106a of the microwave ablation assembly 2200. The cannula 314 has been exposed by application of pressure on the control ring 1400a (FIG. 14A) which overcomes the retaining force imparted by the pins 1020, 1030 (FIG. 10), thus allowing control ring 1400a and locking spindle 1200 (FIG. 12) to move relative to the sliding spindle 600 (FIG. 6). In this position, the microwave assembly 2210 is in a position to perform an ablation.

As described herein, in a preferred embodiment of the present disclosure, the sliding spindle 600, the multi-lumen housing 300, and the microwave transmission and radiation component 100 remain fixed in space (or remain stationary) when the cannula 314, and more particularly the radiating section 106a is deployed to a surgical site or target. The locking spindle 1200, the control ring 1400A, and the nose cone 1800 are drawn in a direction away from the surgical site when the radiating section 106a is deployed to the surgical site or target.

The present disclosure enables placement of a cannula 314, which may be flexible, including radiating section 106a, from a non-radiofrequency transparent access lumen such as cannula 2310 in a variety of interventional procedure types. These interventional procedures include transcutaneous placement (analogous to rigid biopsy kit), open procedure (rigid-needle-like), laparoscopic procedure (hand assisted placement). By use of the cannula 2310 and trocar 2320, an access path to a particular treatment site can be considered separately from the energy delivery device constraints. It is further envisioned that the methods and devices described herein can enable vascular access, whereby a cannula 314, being of flexible construction could be placed with steerable guide-wires. Still further, hybrid procedures utilizing a cannula 314 that is partially rigid and partially flexible are also contemplated.

In accordance with another aspect of the present disclosure, access approaches are envisioned where following placement of the cannula 2310 and removal of the trocar 2320, the cannula 314, which may include steerable guide wires or may be inserted through a flexible guide sheath with steerable guide-wire can extend the access path with 4-dimensional freedom.

The systems and methods of the present disclosure enable an improved workflow by separating the clinician's needs during the access channel placement from the clinician's needs associated with energy delivery. By utilizing the cannula 2310 and trocar 2320 separately, from the microwave ablation assembly 2200, the clinician does not have to deal with constraints of the microwave ablation assembly 2200 while placing the cannula 2310. This removal of the concerns of microwave cables, fluid lines, device weight, handle length, etc., greatly improves the clinician's ability to focus on cannula 2310 placement at or near the target site, and further allows for easier imaging of the placement site (e.g., by fluoroscopy or CT imaging). Still further, because the microwave and fluid componentry is not employed during the cannula 2310 insertion steps, through space savings within the device, the trocar 2320 and cannula 2310 may 'onboard' additional capabilities such as EM navigation sensors, temperature sensors, device fixation features, and other diagnostic capabilities.

In accordance with the present disclosure, the cannula 2310 may have a smaller diameter gauge or French size) than existing devices for placement of microwave ablation components. Indeed, the cannula 2310 may be one of a series of cannulas which are used to dilate the size of the opening in order to receive the microwave ablation assembly 2200.

Detailed embodiments of devices, systems incorporating such devices, and methods using the same as described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in appropriately detailed structure.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

The invention claimed is:

1. A microwave ablation assembly, comprising:
   a first cannula;
   a trocar insertable through the first cannula and configured to facilitate insertion of the first cannula into a target tissue;
   a microwave antenna assembly configured to interlock with the first cannula, the microwave antenna assembly including a coaxial feedline having a radiating section formed thereon, the microwave antenna assembly configured to be inserted into the first cannula;
   a housing coupled to the microwave antenna assembly and including an inflow port and an outflow port, the inflow port and the outflow port configured to receive a fluid for cooling the microwave antenna assembly;
   an actuator operatively connected to one of the first cannula or the microwave antenna assembly and having an outer surface defining an opening therethrough, the actuator disposed around at least a portion of the housing such that the inflow port and the outflow port extend through the opening,
   wherein operation of the actuator between a first position and a second position exposes the radiating section of the microwave antenna assembly from a distal portion of the first cannula.

2. The microwave ablation assembly according to claim 1, further comprising a transition head adapted to connect the microwave antenna assembly to a microwave transmission cable assembly.

3. The microwave ablation assembly according to claim 2, wherein the inflow port provides ingress of the fluid to the housing and the outflow port provides egress of the fluid from the housing.

4. The microwave ablation assembly according to claim 3, further comprising a second cannula extending from the housing, in fluid communication with the inflow and outflow ports, and receiving the microwave antenna assembly, wherein the fluid flows through the second cannula and over the microwave antenna assembly.

5. The microwave ablation assembly system according to claim 3, wherein the transition head includes a first section and a second section, the first section adapted to be coupled to a distal end of a microwave transmission cable assembly and the second section adapted to be coupled to a proximal end of the coaxial feed line.

6. The microwave ablation assembly according to claim 5, further including an o-ring adapted to fit on the second section of the transition head, which is adapted to be received within the housing such that the o-ring forms a fluid tight seal between the second section of the transition head and the housing upon connection.

7. The microwave ablation assembly according to claim 1, wherein the inflow port and the outflow port are parallel to each other, and perpendicular to a longitudinal axis defined by the housing.

8. The microwave ablation assembly of claim 1, further comprising a pair of pins received in a respective pair of recesses on opposing surfaces of the actuator.

9. The microwave ablation assembly according to claim 8, further comprising a locking spindle, wherein the locking spindle is assembled over the actuator.

10. The microwave ablation assembly according to claim 9, wherein the locking spindle further comprises a body portion defining a pair of longitudinal slots on opposing surfaces thereof.

11. The microwave ablation assembly according to claim 10, wherein each longitudinal slot of the pair of longitudinal slots separates a first end of the longitudinal slot from a second end of the longitudinal slot.

12. The microwave ablation assembly according to claim 11, wherein the actuator includes a sliding spindle which is configured to slide within the locking spindle such that the pair of pins travel along the pair of longitudinal slots to lock between the first ends and the second ends.

13. The microwave ablation assembly system according to claim 12, wherein the actuator further includes a control ring assembled over a portion of the locking spindle and the sliding spindle.

14. The microwave ablation assembly according to claim 13, wherein the control ring includes a body portion, a pair of opposing projections extending from the body portion, and a pair of opposing elongated camming surfaces configured and dimensioned to receive the pair of pins and guide longitudinal movement thereof.

15. The microwave ablation assembly according to claim 14, wherein a nose cone is assembled over a portion of the control ring, the nose cone having a proximal end and a distal end, the distal end having a tip portion with a locking mechanism, and the proximal end defining a cut-out portion configured to receive the outflow port therethrough.

16. The microwave ablation assembly according to claim 15, further comprising a retaining ring formed on the locking spindle and configured to secure the nose cone to the locking spindle.

17. The microwave ablation assembly according to claim 14, wherein upon actuation of the actuator, the sliding spindle and second cannula remain stationary, and the first cannula is drawn in the direction of the sliding spindle to expose the second cannula and the radiating section of the microwave antenna assembly located therein.

18. The microwave ablation system according to claim 17, wherein the locking spindle, the control ring, and the nose cone are drawn in the direction of the sliding spindle to expose the second cannula and the radiating section of the microwave antenna assembly located therein.

19. A microwave ablation assembly, comprising:
   a cannula defining a lumen;
   a microwave antenna configured to be inserted through the lumen defined by the cannula;
   an actuator coupled to the microwave antenna and having a housing configured to interlock with the cannula upon insertion of the microwave antenna through the lumen, the actuator movable to position a radiating section of the microwave antenna distal to a distal end of the cannula for treating tissue;
   an inflow port extending through an opening defined through an outer surface of the housing of the actuator and configured to provide ingress of a fluid for cooling the microwave antenna; and
   an outflow port extending through the opening defined through the outer surface of the housing of the actuator and configured to provide egress of the fluid.

* * * * *